(12) United States Patent
Welch et al.

(10) Patent No.: US 8,999,703 B2
(45) Date of Patent: Apr. 7, 2015

(54) CELL CONTAINER

(76) Inventors: Daniel P. Welch, Zimmerman, MN (US); John R. Wilson, New Brighton, MN (US)

(*) Notice: Subject to any disclaimer, the term of this patent is extended or adjusted under 35 U.S.C. 154(b) by 1109 days.

(21) Appl. No.: 12/115,353

(22) Filed: May 5, 2008

(65) Prior Publication Data

US 2009/0272748 A1 Nov. 5, 2009

(51) Int. Cl.
| | |
|---|---|
| C12M 1/24 | (2006.01) |
| C12M 3/00 | (2006.01) |
| A01N 1/02 | (2006.01) |
| C12M 1/00 | (2006.01) |
| C12M 1/34 | (2006.01) |

(52) U.S. Cl.
CPC ............. *A01N 1/0273* (2013.01); *C12M 23/08* (2013.01); *C12M 23/38* (2013.01); *C12M 41/44* (2013.01)

(58) Field of Classification Search
CPC .... A01N 1/0273; C12M 41/44; C12M 23/08; C12M 23/38
USPC ...................... 435/283.1, 304.1; 220/304, 501
See application file for complete search history.

(56) References Cited

U.S. PATENT DOCUMENTS

| | | | |
|---|---|---|---|
| 4,321,330 A | 3/1982 | Baker et al. | |
| 4,534,483 A | 8/1985 | Kassis et al. | |
| 4,578,588 A | 3/1986 | Galkin | |
| 4,650,086 A | 3/1987 | Morrison, Jr. | |
| 4,952,510 A | 8/1990 | Gabridge | |
| 5,154,112 A | 10/1992 | Wettern | |
| 5,615,791 A | 4/1997 | Vatelot et al. | |
| 5,728,576 A * | 3/1998 | Dudley et al. | 435/283.1 |
| 5,856,176 A | 1/1999 | Mathus et al. | |
| 5,945,075 A | 8/1999 | Chiron et al. | |
| 6,015,534 A | 1/2000 | Atwood | |
| 6,053,888 A | 4/2000 | Kong | |
| 6,337,052 B1 | 1/2002 | Rosenwasser | |
| 6,375,028 B1 | 4/2002 | Smith | |
| 6,410,310 B1 | 6/2002 | Flegal et al. | |
| 6,468,788 B1 | 10/2002 | Marotzki | |
| 6,622,882 B2 | 9/2003 | Smith | |
| 7,033,821 B2 | 4/2006 | Kim et al. | |
| 7,273,750 B1 | 9/2007 | Olivier et al. | |
| 7,387,216 B1 | 6/2008 | Smith | |
| 2002/0130100 A1 | 9/2002 | Smith | |
| 2002/0170916 A1 | 11/2002 | Crouch et al. | |

(Continued)

FOREIGN PATENT DOCUMENTS

| | | |
|---|---|---|
| JP | 2005516596 A | 6/2005 |
| JP | 2006217845 A | 8/2006 |
| JP | 2007511205 A | 5/2007 |
| JP | 2007269327 A | 10/2007 |

(Continued)

OTHER PUBLICATIONS

European Search Report from European Application No. EP08769296 dated Feb. 12, 2013.

(Continued)

*Primary Examiner* — Michael Hobbs
(74) *Attorney, Agent, or Firm* — Patterson Thuente Pedersen, P.A.

(57) ABSTRACT

This invention relates to methods and devices that improve the process of culturing cells and/or shipping cells from one location to another. They have the capacity to reduce the risk of contamination, regulate pressure in the medium surrounding cells, and maintain cells in a uniform distribution throughout transit. This leads to an improved level of process control relative to current methods.

20 Claims, 12 Drawing Sheets

(56) References Cited

U.S. PATENT DOCUMENTS

| | | |
|---|---|---|
| 2003/0130100 A1 | 7/2003 | Perez |
| 2005/0084954 A1* | 4/2005 | Bader ........................ 435/295.1 |
| 2005/0239197 A1 | 10/2005 | Katerkamp et al. |
| 2007/0026517 A1* | 2/2007 | Schulz et al. ................. 435/325 |
| 2008/0245676 A1 | 10/2008 | McManus et al. |
| 2008/0251490 A1 | 10/2008 | Livingston et al. |
| 2009/0139992 A1 | 6/2009 | Breidenthal et al. |

FOREIGN PATENT DOCUMENTS

| | | |
|---|---|---|
| JP | 2009205548 A | 9/2009 |
| WO | WO00/17315 | 3/2000 |
| WO | WO 2007/015770 A1 | 2/2007 |

OTHER PUBLICATIONS

Office Action from related Canadian Application 2722907, dated Jun. 23, 2014, 3 pgs.

* cited by examiner

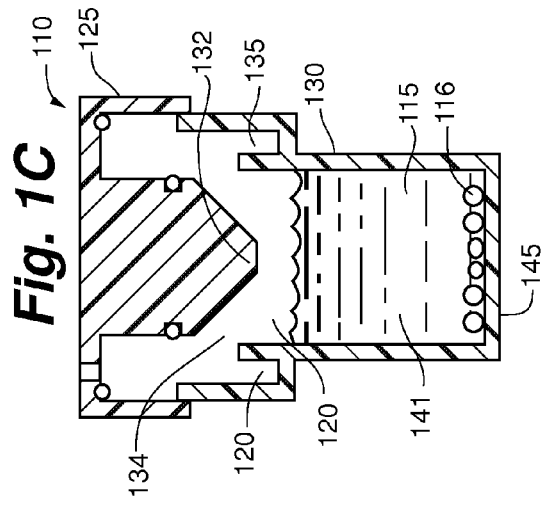
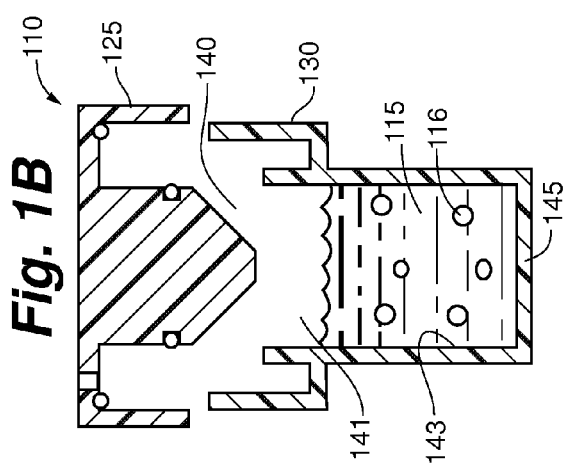
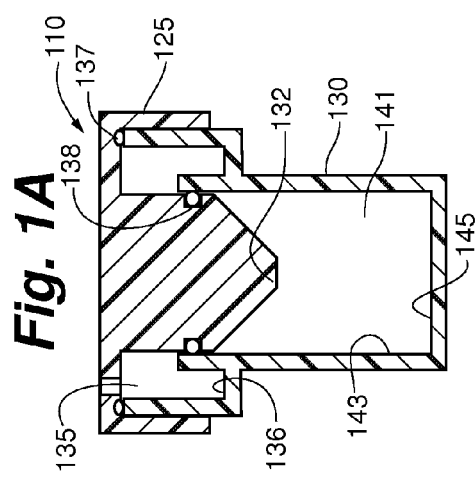
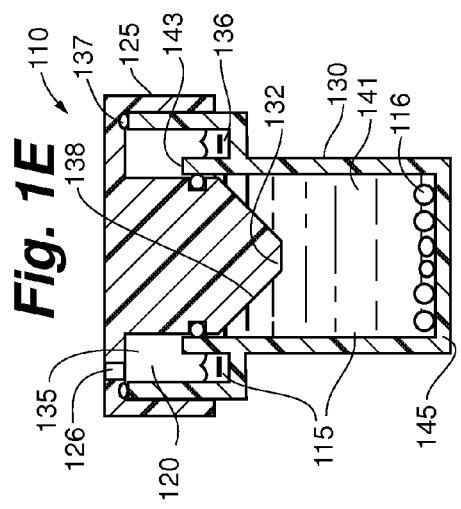
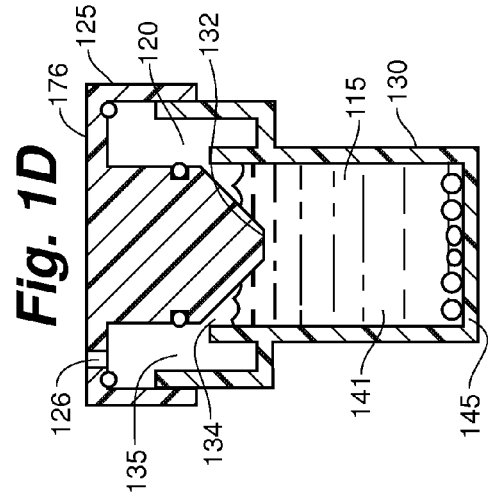

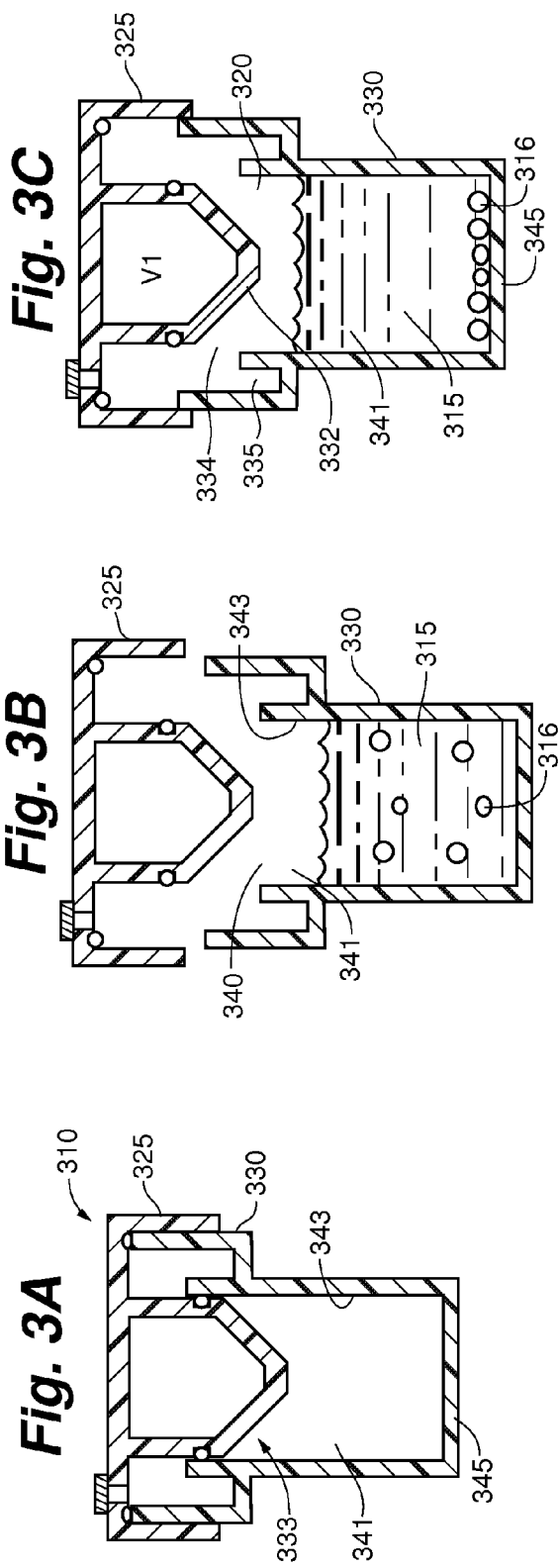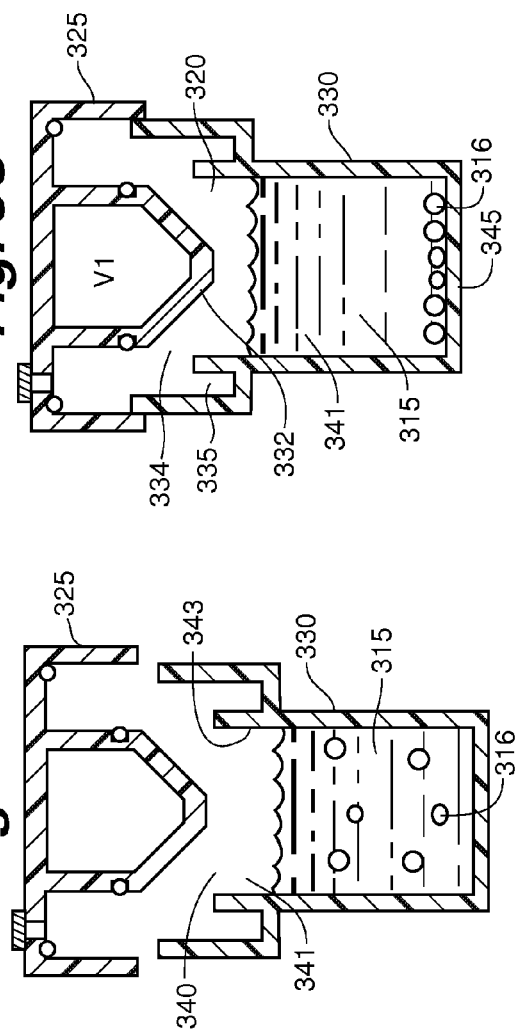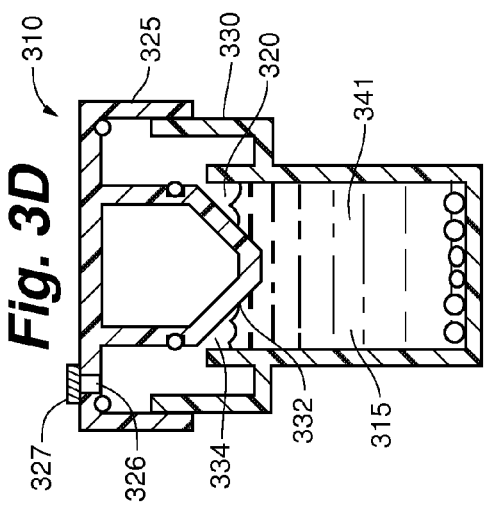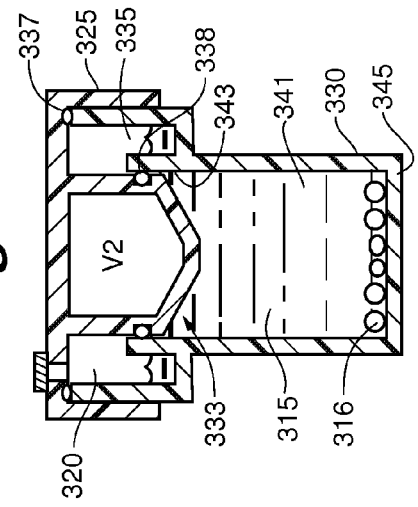

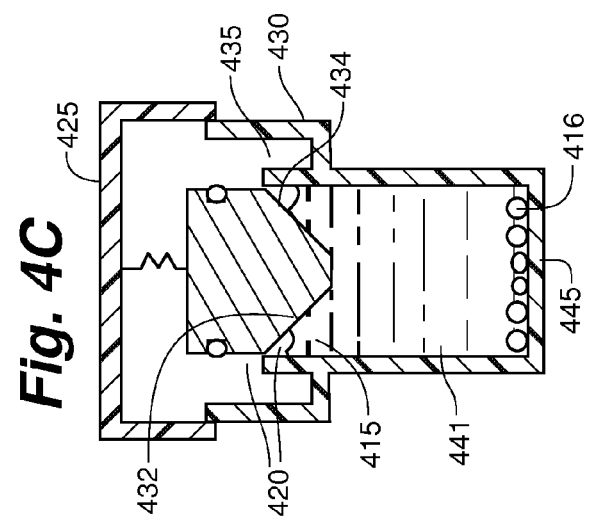
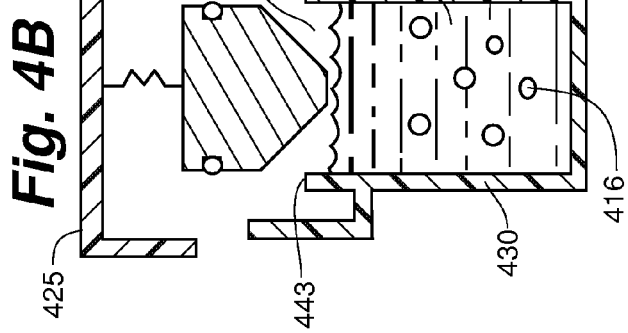
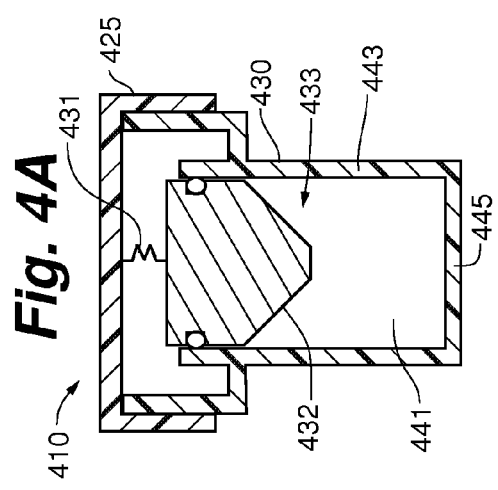
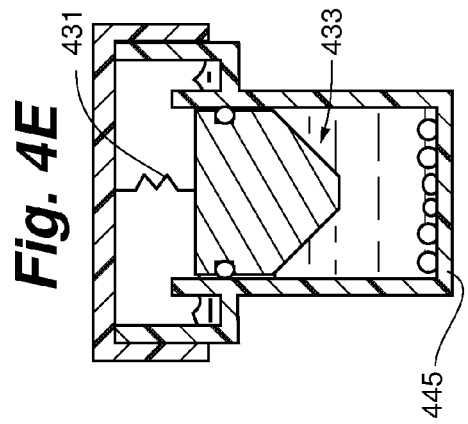
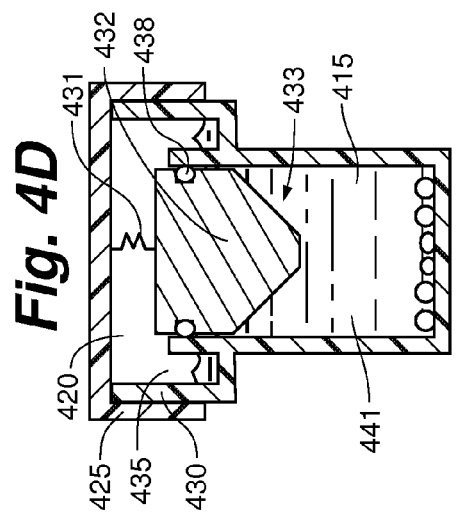

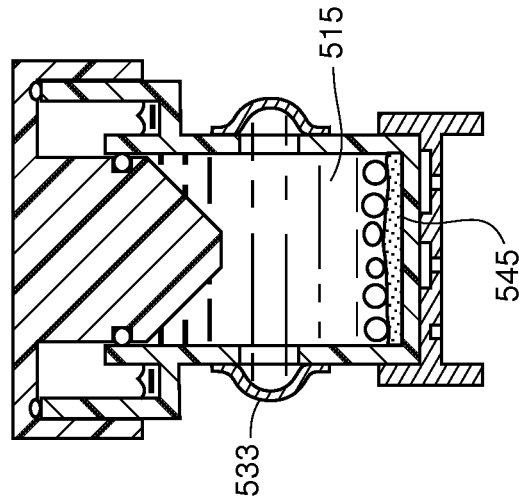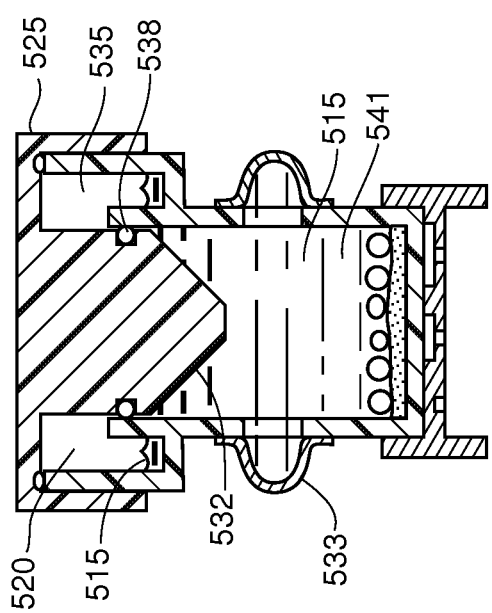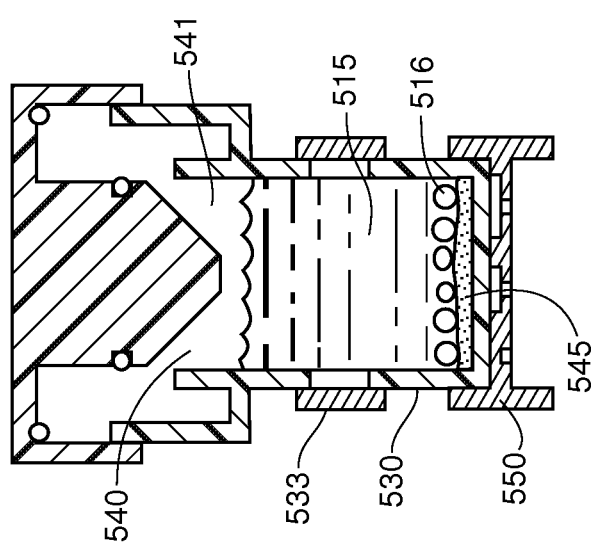

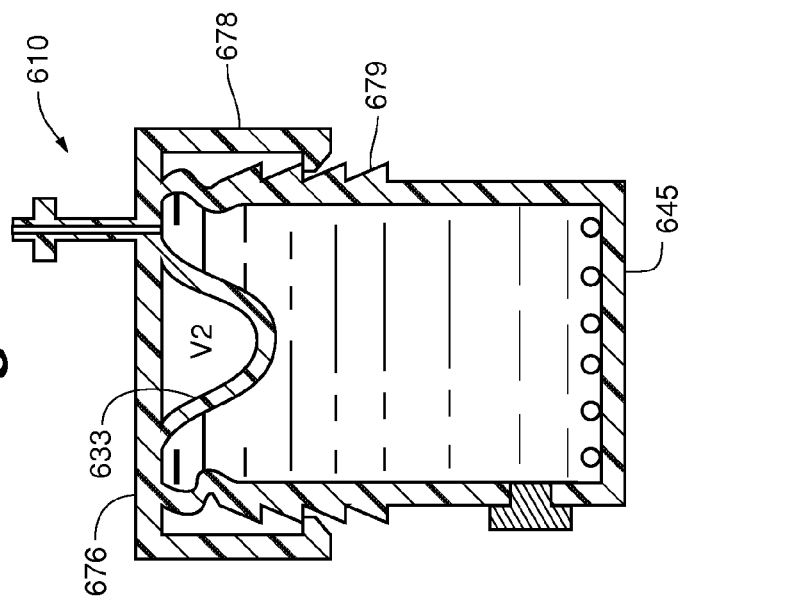
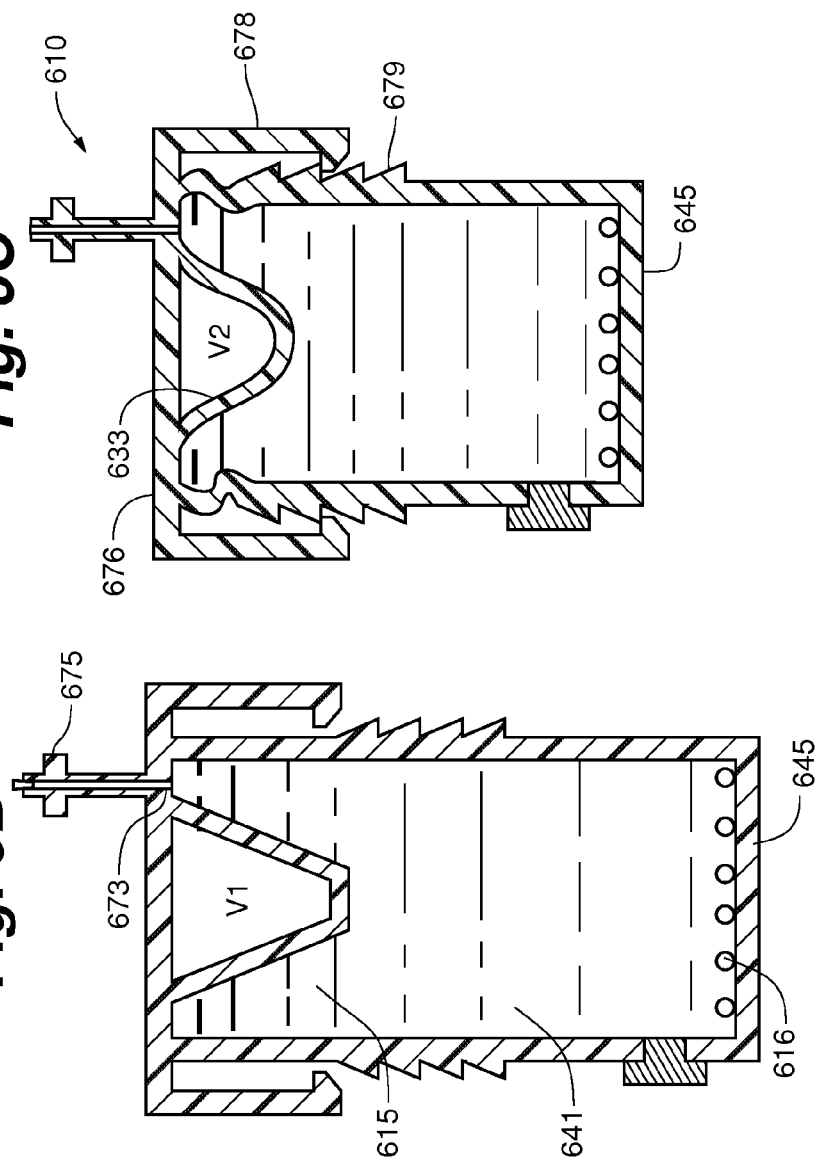
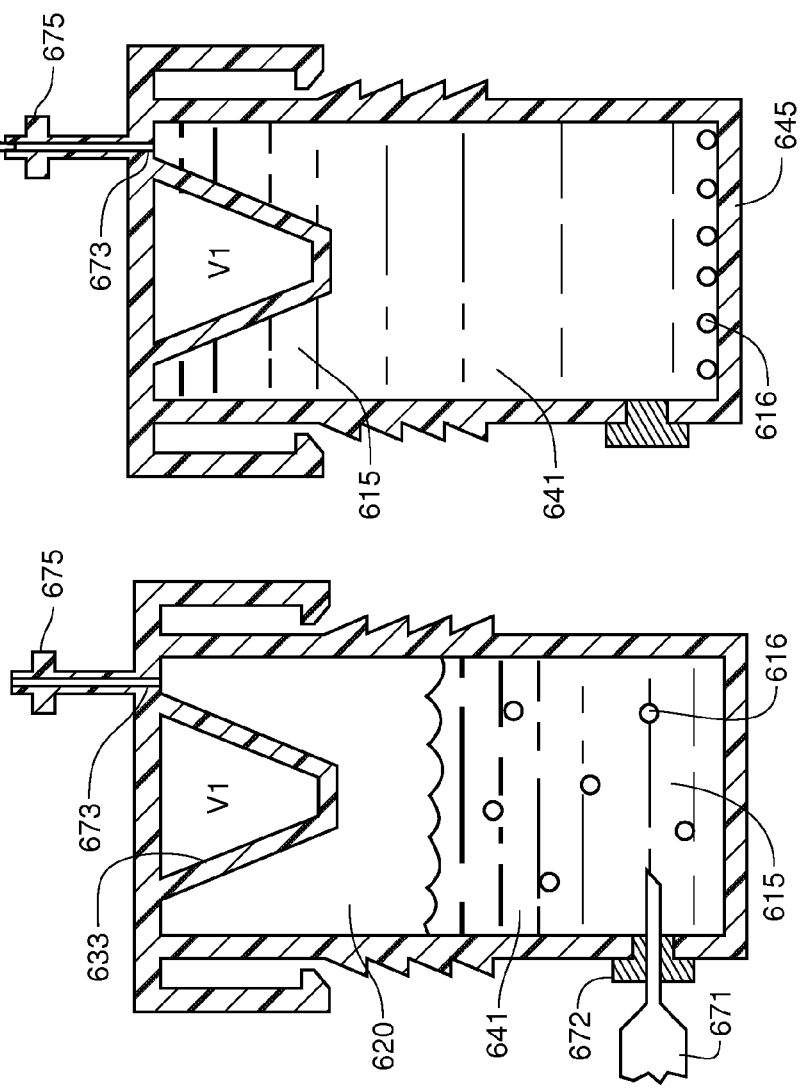

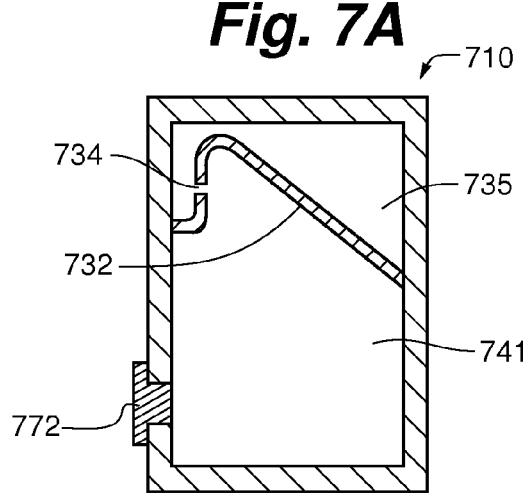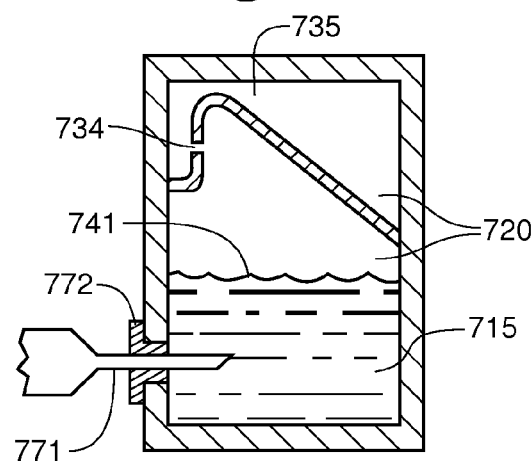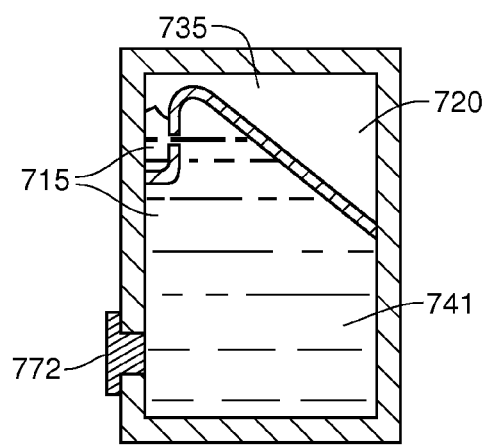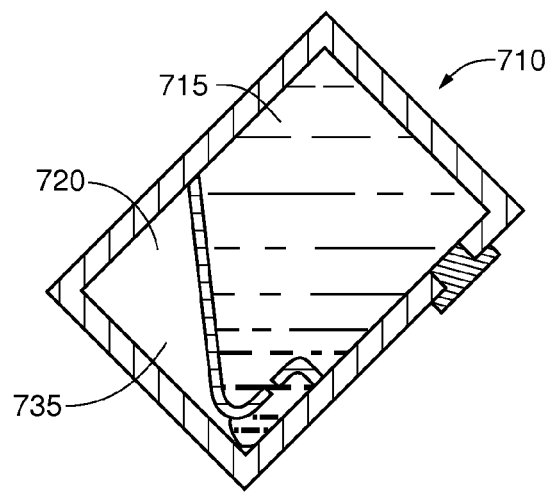

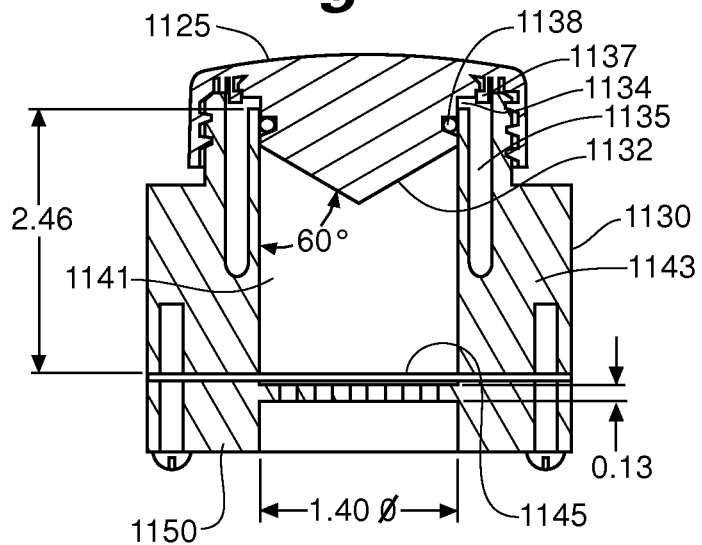
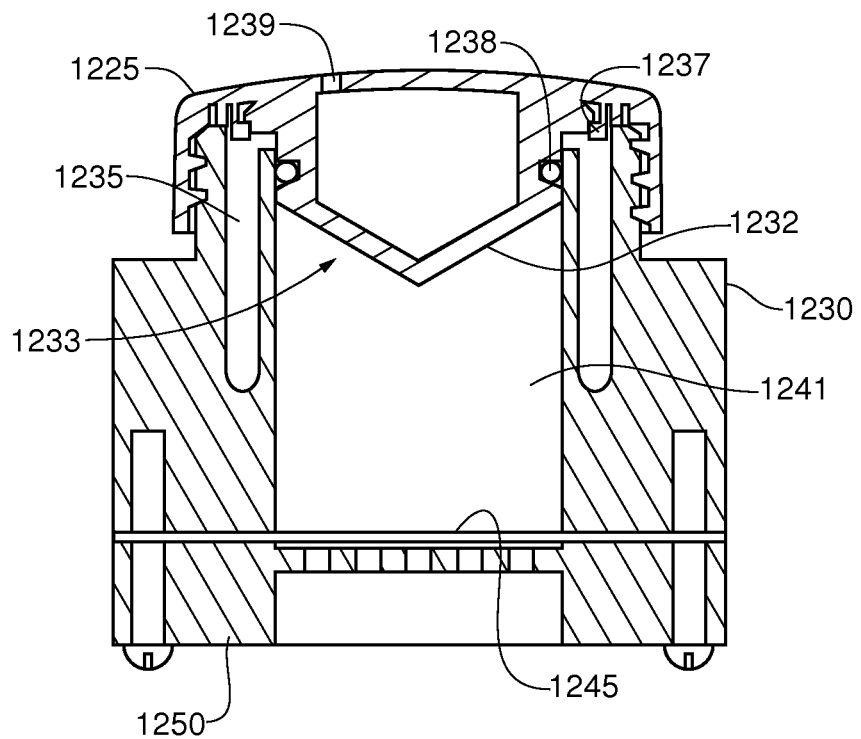

CELL CONTAINER

GOVERNMENT INTERESTS

This invention was made in part with U.S. Government support under National Institutes of Health Small Business Innovative Research Grant DK0659865 "Islet culture, shipping, and infusion device". The U.S. Government may have certain rights in this invention.

RELATED APPLICATION

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, and, each of these documents or references ("herein-cited references"), as well as each document or reference cited in each of the herein-cited references (including any manufacturer's specifications, instructions, etc.), is hereby expressly incorporated herein by reference. Reference is also made to co-pending U.S. application Ser. No. 10/961,814 (Wilson et al. '814), co-pending U.S. application Ser. No. 11/952,848 (Wilson '848), and co-pending U.S. application Ser. No. 11/952,856 (Wilson et al. '856) which are hereby incorporated herein by reference.

TECHNICAL FIELD

The technical field of the invention relates to methods and devices that improve the process of removing gas and controlling pressure in containers, with a focus on providing benefit over the current approaches used in the biotechnology industry. The disclosed devices and methods improve the process of culturing and/or shipping cells. Attributes include the capacity to reduce the risk of contamination, respond to temperature driven medium volume changes in order to minimize undesirable pressure effects, maintain cells in a uniform distribution throughout transit, reduce cell surface density throughout transit, and expose cells to ambient oxygen throughout the culture and shipping process. This leads to an improved level of process control relative to current devices and methods.

DISCUSSION OF LIMITATIONS OF CONVENTIONAL TECHNOLOGIES DESCRIBED IN RELATED ART

Advances in cell therapies have created an increasing need to ship cells from one location to another. For example, when islet research or islet transplants are undertaken, it is common for the islets to be recovered from a pancreas and cultured at one location, then shipped to a different location for research or clinical use. Existing methods and devices used to house cells during shipping do not lend themselves to good process control. Cells are typically placed in conical tubes or flasks, packaged in a Styrofoam™ container that includes ice or cold packs, and shipped to another location. This can damage cells since there is little control over a variety of variables that can affect their quality.

In general, the conditions experienced by cells during shipping can deviate markedly from the controlled conditions present during culture. For example, in the case of islets, they are consolidated from many flasks in which they are cultured, into far fewer flasks or conical tubes for shipping. This greatly increases islet surface density, often many times beyond that of the culture stage. Normally they are cultured at surface density that does not exceed 200 islets/cm$^2$. At higher density, competition for nutrients and oxygen is increased and islets can diminish in health. Furthermore, islets can aggregate at high density. When shipping cells, flasks or conical tubes are typically filled entirely with medium in order to displace all the gas, which could otherwise damage the cells. Thus, the vessels are filled to the very top of their access ports with medium before their caps are attached. This leads to an elevated risk of contamination. Removing gas greatly limits the amount of oxygen available to cells. To compensate for this, the cells are typically shipped in the presence of cold packs to slow down the metabolic activity of the cells and diminish oxygen demand. When medium attempts to contract in volume as it cools within the sealed container that the cells reside in, pressure is exerted on the walls of the container, placing the walls under stress. This can cause cracks or leaks in the container, particularly when using flasks. It can also de-gas the medium. Thus, there are a wide variety of deficiencies with existing devices.

It is an object of the present invention to disclose improved devices and methods for shipping cells that minimize contamination risk, create an environment that more closely mimics the culture environment, allow cells to reside in a uniformly distributed pattern, relieve stress on the walls of the device, minimize de-gassing of the medium, and allow reduced cell surface density.

The recent emergence of devices that rely on gas permeable membranes to eliminate of the need for a gas-liquid interface to perform gas exchange has led to an increased need to control where gas can reside in such a device. Recent patent applications attempt to rectify this problem by adding features that require awkward manipulation of the devices. It is also an object of the present invention to provide superior gas removal features that do not require awkward manipulation to function.

SUMMARY OF THE INVENTION

According to the present invention, certain embodiments disclosed herein allow gas to be displaced from the cell container without need of filling the container entirely with medium. The cell container includes a fluid displacement member, an overflow reservoir, and a fluid exit path allowing fluid to move from the cell compartment to the overflow reservoir.

In one aspect of the present invention, the cell container includes structure for moving the fluid displacement member into the cell compartment. Embodiments that accomplish this include open and closed systems.

In a preferred open system embodiment for displacing unwanted gas, a fluid displacement member is attached to a cap. The body of the device includes an overflow reservoir. The cap and body are designed to be screwed together, providing structure for moving the fluid displacement member into the cell compartment with a high degree of resolution. By moving the fluid displacement member into the cell compartment, it can displace residual gas and leave the cell compartment entirely filled with medium. The overflow reservoir can be structured to retain any medium that has been displaced from the cell compartment when the cap is removed. This embodiment can be integrated into conical tubes or flasks, and preferably into structures that allow cells to uniformly settle and reside upon a flat surface.

In a closed system embodiment for displacing gas, medium can be delivered into the cell compartment by way of a septum. The cell container includes structure to drive a fluid displacement member into the cell compartment and displace unwanted gas into an overflow reservoir. In an illustrative embodiment, cell container comprises such structure in its body in the form of fingers that interlock with tangs to change the height of the cell container.

In a closed system embodiment for displacing gas, a method is disclosed that delivers pressurized medium into the cell compartment to drive gas from the cell compartment without need of structure to physically move the fluid displacement member. The shape of the overflow reservoir creates the fluid displacement member. Pressurized medium is driven into the cell compartment, forcing gas into the overflow reservoir by way of a fluid exit path.

In another aspect of the present invention, pressure within the cell compartment is regulated by use of a cell compartment volume adjustment feature. The cell compartment volume adjustment feature includes structure that allows it to move in response to forces acting upon it. A wide variety of structures are illustrated that allow the cell compartment volume adjustment feature to move, including flexible, hermetically sealed hollow bodies, elastomeric cell compartment walls, and solid bodies attached to springs. These types of structures allow the cell compartment volume adjustment feature to automatically act to decrease or increase the volume of the cell compartment in order to mitigate changes in pressure caused by external events such as temperature change or ambient pressure change. For optimal performance, the cell compartment volume adjustment feature should be placed in an initial pre-determined state of potential energy. According to one aspect, the cell container includes structure that acts to alter the overall geometry of the cell container to place the cell compartment adjustment feature in a desired initial state of potential energy. Many of the cell container structures that are available to place the cell compartment volume adjustment feature in a desired state of initial potential energy are the same as those available to drive the fluid displacement member into the cell compartment. According to another aspect, methods for placing the cell compartment adjustment feature in a desired initial state of potential energy, absent structure to alter the overall geometry of the cell container, are disclosed. In this aspect, pressurized medium performs that task. The benefit of the cell compartment adjustment feature is a more controlled environment in the cell compartment relative what can be attained in traditional devices.

In another aspect, the fluid displacement member is structured to become a cell compartment volume adjustment feature.

In another aspect, the overflow reservoir is structured to become a cell fluid displacement member.

In another aspect, the overflow reservoir is structured to become a cell compartment volume adjustment feature.

Another embodiment discloses a baffle to prevent cells from accumulating in an undesirable, non-uniformly distributed surface density upon the lower wall of the device.

Any embodiment can allow cells to reside in a uniform distribution in proximity of a gas permeable wall that allows gas exchange with ambient gas.

Certain devices and methods disclosed herein allow cells to reside upon more than one scaffold during culture and/or shipping to minimize device footprint while providing the ability to purge gas from the device, minimize the potential for accumulation of gas in unwanted areas of the device, reduce stress on the walls of the device, and allow reduced cell surface density.

Certain methods disclosed herein allow cells to reside in a uniform distribution throughout transit by use of a gimbal, minimizing the potential for undesirable high density accumulation.

BRIEF DESCRIPTION OF THE DRAWINGS

FIG. 1A illustrates a cross-sectional view of an embodiment of a cell container that reduces contamination risk while allowing gas to be displaced from the cell compartment, without need of filling the cell compartment entirely with medium. A cap includes a fluid displacement member and is attached to the body of the cell container, which includes a cell compartment and an overflow reservoir.

FIG. 1B shows the cap removed from the body and medium and cells residing as a mixed suspension in the cell compartment. Gas resides within the cell compartment.

FIG. 1C shows the cap being attached to the body of the cell container and cells residing in a uniform distribution upon the lower wall of the cell compartment.

FIG. 1D shows the cap being lowered onto the body of the cell container and the fluid displacement member making contact with, and displacing, gas and medium. Gas moves from the cell compartment via a fluid exit path.

FIG. 1E shows the cap fully attached to the body of the cell container. Gas has been displaced from the cell compartment and a small amount of medium has come to reside in the overflow reservoir.

FIG. 3A illustrates a cross-sectional view of an embodiment of a cell container that includes a hollow cell compartment volume adjustment feature. In this embodiment, the cell compartment volume adjustment feature performs the role of displacing gas and regulating pressure. A cap, including the cell compartment volume adjustment feature and gas displacement member, is attached to the body of the cell container. The body includes a cell compartment and an overflow reservoir.

FIG. 3B shows the cap removed from the body and medium and cells residing as a mixed suspension in the cell compartment. Gas resides within the cell compartment.

FIG. 3C shows the cap being attached to the body of the cell container and cells residing in a uniform distribution upon the lower wall of the cell compartment.

FIG. 3D shows the cap being lowered onto the body of the cell container and the fluid displacement member making contact with, and displacing, gas and medium. Gas moves from the cell compartment via a fluid exit path.

FIG. 3E shows the cap fully attached to the body of the cell container. Gas has been displaced from the cell compartment and a small amount of medium has come to reside in the overflow reservoir. The cell compartment volume adjustment feature has been placed in a desired state of potential energy as it has compressed its internal volume in response to the force of medium acting upon it.

FIG. 4A illustrates a cross-sectional view a cell container that includes another embodiment of a cell compartment volume adjustment feature. In this embodiment, the cell compartment volume adjustment feature includes a solid body and a spring that act to perform the role of displacing gas and regulating pressure. The cell compartment volume adjustment feature is attached to a cap with the spring. The cap is attached to the body of the cell container, which includes a cell compartment and an overflow reservoir.

FIG. 4B shows the cap removed from the body and medium and cells residing as a mixed suspension in the cell compartment. Gas resides within the cell compartment.

FIG. 4C shows the cap being attached to the body of the cell container and cells residing in a uniform distribution upon the lower wall of the cell compartment.

FIG. 4D shows the cap being lowered onto the body of the cell container and the fluid displacement member making contact with, and displacing, gas and medium. Gas moves from the cell compartment via a fluid exit path. The spring of the cell compartment volume adjustment feature has begun to compress due to the force exerted by medium.

FIG. 4E shows the cap fully attached to the body of the cell container. Gas has been displaced from the cell compartment and a small amount of medium has come to reside in the overflow reservoir. The cell compartment volume adjustment feature has been placed in a desired state of potential energy as its spring has compressed in response to the force of medium acting upon it.

FIG. 5A shows a cross-sectional view of another embodiment of a cell container configured with a cell compartment volume adjustment feature. A cap includes a fluid displacement member. The body includes an overflow reservoir, a flexible wall that acts as a cell compartment volume adjustment feature, and a lower wall support. The cap is being lowered onto the body. Gas, medium, and cells reside in the cell compartment.

FIG. 5B shows the cap moving to a final position. The fluid displacement member has displaced gas and a small amount of medium from the cell compartment into the overflow reservoir, and the force exerted by the fluid displacement member onto the medium has driven the volume adjustment feature to an initial state of potential energy.

FIG. 5C shows the changed shape of the volume adjustment feature after it has reduced its potential energy in response to medium cooling.

FIG. 6A shows a cross-sectional view of a closed system embodiment of a cell container that includes a cell compartment volume adjustment feature. The vented cell container includes finger locks and tangs as structure for changing its overall shape. Medium and cells are introduced into the cell compartment by needle penetration of a septum. Gas is displaced via a sterile vent.

FIG. 6B shows the cell compartment entirely filled with medium. The cell compartment volume adjustment feature has an internal volume identified as V1.

FIG. 6C shows the volume of the cell compartment having been reduced as fingers latch onto tangs. The cell compartment volume adjustment feature has collapsed to an internal volume identified as V2, thereby assuming a desired state of potential energy.

FIG. 7A shows a cross-sectional view of a closed system embodiment of a cell container that includes a fluid displacement member, an overflow reservoir, a fluid exit path connected the cell compartment to the overflow reservoir.

FIG. 7B shows a needle penetrating the septum to deliver medium. Gas moves through the fluid exit path into the overflow reservoir. Medium resides in the cell compartment.

FIG. 7C shows gas and a small amount of medium residing in the overflow reservoir, and medium filling the cell compartment.

FIG. 7D shows the cell container oriented to a new position and gas remaining trapped in the overflow reservoir.

FIG. 11 shows a test fixture used to demonstrate the function of a structure for moving a fluid displacement member into a cell compartment in a manner that displaced gas and a small amount of medium into an overflow reservoir. The cell container includes a cap, body, fluid displacement member, overflow reservoir, fluid exit path, and a cell compartment.

FIG. 12 shows how the test fixture of FIG. 11 was adapted to automatically adjust the volume of the cell compartment as medium changed temperature. The fluid displacement member was structured as a flexible, hermetically sealed hollow body.

DETAILED DESCRIPTION OF THE INVENTION

Figure 2:
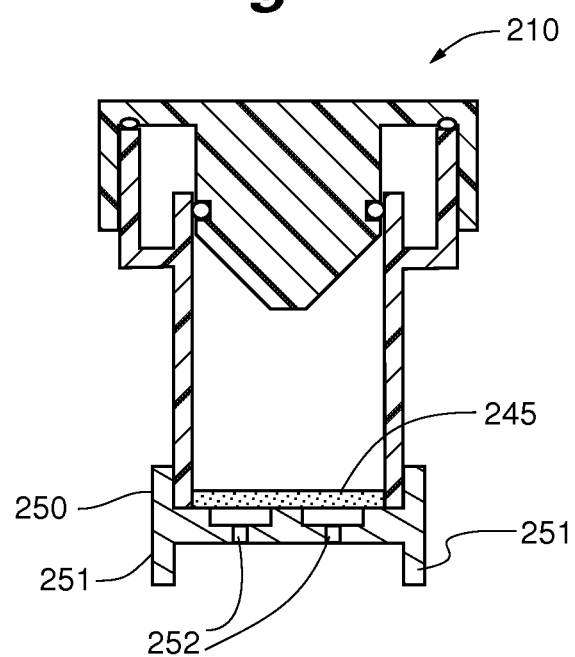
FIG. 2 illustrates a cross-sectional view of an embodiment in which the cell container includes a lower wall comprised of gas permeable material and a lower wall support to allow the cells to be maintained in a uniform distribution upon a gas permeable surface.

FIG. 1A, FIG. 1B, FIG. 1C, FIG. 1D, and FIG. 1E show cross-sectional views of cell container 110, which is configured to displace gas from the cell compartment 141 by merely attaching cap 125. A cross-section of cell container 110 is shown in FIG. 1A. Cap 125 is secured to body 130. Fluid displacement member 132, sidewall(s) 143, and lower wall 145 bound cell compartment 141 and define the volume of cell compartment 141. Overflow reservoir 135 is present about the perimeter of fluid displacement member 132. In FIG. 1B, cap 125 is separated from body 130 to expose cell compartment 141. Medium 115 and cells 116, in this depiction shown as a well mixed suspension, have been placed into cell compartment 141 by way of access port 140. Unlike conventional methods that rely on flasks or conical tubes, this device does not need to have medium reside all the way to the top of the access port in order for gas to be displaced from the cell compartment. Instead, medium 115 can reside at a level well below access port 140, thereby reducing the risk of contamination. Lower wall 145 can be any shape. For example, it can be a tapered shape of a conical tube. Hereinafter, the lower wall is synonymous with the bottom of the cell compartment. Thus, it need not be a distinct wall from sidewalls 143, just a lower surface of cell compartment 141 upon which medium can reside. For example, sidewall 143 could be a cone shape, the walls meeting at a point forming the lower wall. In this depiction, lower wall 145 is shown as a flat surface. A flat surface is preferred, as it allows cells to spread out as they gravitate to the lower wall, minimizing potential deleterious effects of high surface density. As shown in FIG. 1C, cap 125 has come in contact with body 130. Cells 116 have gravitated to distribute uniformly upon lower wall 145 of cell compartment 141. Gas 120 resides above medium 115. Gas 120 also occupies overflow reservoir 135 and fluid exit path 134. Fluid exit path 134 is the space between fluid displacement member 132 and overflow reservoir 135. Fluid displacement member 132 is attached to cap 125 and resides in a first position at a first distance from the lowest surface of cell compartment 141, in this case a flat lower wall 145. Cell container 110 is positioned to displace unwanted gas by the act of reducing the distance between fluid displacement member 132 and lower wall 145. FIG. 1D shows the distance between fluid displacement member 132 and lower wall 145 being reduced as cap 125 moves downward upon body 130. Preferably, when a cap and a body are included in the cell container, the structural relationship between the cap and the body allows the cap to be lowered onto the body in a way that controls the distance that the fluid displacement member moves into the cell compartment. When the cap and body are threaded, this allows an excellent structural means to control the distance at which the fluid displacement member resides above, or within, the cell compartment. Fluid displacement member 132 is shown in contact with medium 115, displacing medium 115. The upper surface of medium 115 has risen in the direction of fluid exit path 134 and a portion of gas 120 has moved out of cell compartment 141 via fluid exit path 134. Fluid exit path 134 is the space through which fluid that is displaced by fluid displacement member 132 moves. There are a variety of ways to handle the gas that is displaced from cell compartment 141. Preferably, to remove all gas, at least a portion of fluid displacement member 132 should reside lower than fluid exit path 134 so the gas will rise to fluid exit path 134 as it is displaced. Gas can be displaced to the ambient atmosphere by structuring cap 125 so that it allows gas to vent between it and body 130 as cap 125 moves downward upon body 130. Alternatively, vent 126 can be present to allow gas to be displaced through upper wall 176. Preferably, vent 126, if present, will be capable of being open or closed, and more preferably be covered by a sterile filter, such as a 0.2 micron microporous filter. Vent 126 is shown only to illustrate one possible location in which it could reside. In the absence of a vent for gas to move to ambient, the volume of overflow reservoir 135 can be made to be an appropriate size to accommodate displaced gas 120. FIG. 1E shows how gas 120 and a small amount of medium 115 have been displaced into overflow reservoir 135 when cap 125 is in its final resting position upon body 130. This is a result of fluid displacement member 132 having a shape that displaces gas, and potentially a relatively small amount of medium, into overflow reservoir 135 as it enters the cell compartment 141 and moves closer to the lowest portion of cell compartment 141. As fluid displacement member 132 enters medium 115, the level of medium 115 rises and drives gas 120 through fluid exit path 134 and into overflow reservoir 135, where it can be vented into atmosphere or collected within overflow reservoir 135. In general, the perimeter of fluid displacement member 132 preferably conforms to the perimeter of cell compartment 141 and fluid displacement member 132 includes a tapered wall that directs fluid towards the perimeter of cell compartment 141. The tapered wall would include one portion that is lower than another portion of the wall. Stated differently, the wall of fluid displacement member 132 that is intended to contact medium is not entirely horizontal. When cell compartment 141 is cylindrical, a conical shape for fluid displacement member 130 is preferred, since its tapered shape allows uniform displacement of fluid about its perimeter. Preferably, overflow reservoir 135 surrounds cell compartment 141, ensuring any medium displaced by fluid displacement member 132 resides in overflow reservoir 135. If medium were to be displaced onto the outside of body 130, it would become contaminated. Even though the contents of cell container 110 could be contamination free, this could expose those handling the device to contaminants, virus, and the like. Thus, overflow reservoir 135 is not required, but is preferred. Although depicted as such in this illustrative embodiment, cell compartment sidewall 143 need not be higher than lowest overflow reservoir surface 136. So long as the height of the outer wall of cell container body 130 exceeds that of lowest overflow reservoir surface 136, when fluid displacement member 132 enters medium 115, medium need not spill out of the cell container, as best shown in FIG. 1E. The optimal difference in height between the outer wall of body 130 and lower overflow reservoir surface 136 increases as the volume of medium 115 that is expected to be displaced from cell compartment 141 increases. When there is a desire to ensure that all gas 120 is displaced from cell compartment 141, preferably the volume of space that fluid displacement member 132 occupies within cell compartment 141 is of slightly greater volume than the volume of space occupied by gas 120 that needs to be displaced from cell compartment 141. Thus, a preferred design allows a small amount of medium 115 to be displaced into overflow reservoir 135 in order to ensure that all gas 120 is removed. If the distance between fluid displacement member 132 and cell compartment sidewall 143 is small enough, the ability for gas to re-enter cell compartment 141 is virtually eliminated regardless of the position in which cell container 110 is oriented during shipping. A distance of less than about 0.05 inches is preferred, and more preferably 0.02 inches or less, as a narrow distance will substantially inhibit the ability for gas to re-enter the cell compartment. As an alternative to a limited distance between fluid displacement member 132 and cell compartment sidewall 143, a seal between fluid displacement member 132 and cell compartment 141 can be provided, such as cell compartment seal 138, in this depiction shown as an o-ring. Preferably, contaminants are prevented from contacting any medium that may come to reside in overflow reservoir 135, particularly in the absence of cell compartment seal 138. In this depiction, overflow reservoir seal 137, shown as an o-ring, is present and has sealed body 130 to cap 125 when cap 125 is in the closed position. To prevent contamination, vent 126 would either be closed, sterile filtered, a tortuous path, or not present.

There may be a desire to prevent medium that has been displaced from the cell compartment from re-entering the cell compartment when the cap is removed from the cell container. By structuring the height of cell compartment sidewall 143 to exceed the height of lowest overflow reservoir surface 136 about the perimeter of cell compartment 141, medium 115 that was initially displaced from cell compartment 141 can be prevented from returning to cell compartment 141 when cap 125 is removed. The optimal height of cell compartment sidewall 143 depends on the volume of medium that is expected to be displaced into overflow reservoir. The top of cell compartment sidewall 143 should exceed the height at which medium is expected to reside above lowest overflow reservoir surface 136.

Cell container 110 can be configured to allow gas exchange between cells 116 and the external environment by making any of the walls gas permeable. To place the cells in the best location for oxygen access, preferably lower wall 145 of cell compartment 141 is flat and is comprised of gas permeable material. The gas permeable material used to allow gas transfer into and out of the device can be comprised of any membrane, film, material, or combination of materials used, or previously described for use, in gas permeable cell culture devices, such as silicone, flouroethylenepolypropylene, polyolefin, polystyrene film, ethylene vinyl acetate copolymer and those that include fluorine. Many sources for learning about gas permeable materials and their use in cell culture are available for guidance, including but not limited to U.S. Pat. Nos. 5,693,537, 6,455,310, 6,297,046, International Publication Number WO 01/92462, and Wilson et al. '814. Silicone is a particularly good choice of material for applications in which the cells have moderate to high oxygen demand. For example, as described in Wilson et al. '814, we have found that the use of dimethyl silicone with a thickness less than or equal to about 0.033 inches thick, and more preferably 0.0045 inches thick, is a good choice when culturing cells, and therefore will be useful for shipping cells in a well oxygenated state. The advantage of increasing medium height beyond the conventional height of 1.0 cm associated with devices that integrate a lower gas permeable membrane, and 2.0 cm in gas permeable devices that integrate lower and upper gas permeable membranes, is also described in Wilson et al. '814. Thus, when the height of cell compartment sidewall 143 is greater than 1.0 cm, and lower wall 145 is comprised of gas permeable material, more cells can be supported than traditional gas permeable devices allow. In a preferred embodiment, the lower wall is gas permeable and a cell compartment sidewall exceeds a height of 1.0 cm. Also, preferably the cell compartment sidewalls are generally perpendicular to the gas permeable lower wall so that cells settle uniformly upon the lower wall during gravitational seeding from a well mixed cell suspension. The optimal surface area of the lower wall that is comprised of gas permeable material depends on the oxygen transmission rate of the material and the oxygen demand of the cells. In the case where there is a desire to culture and/or ship cells or tissue that exhibit high oxygen demand, such as islets, the surface area should be maximized so that each cell, or islet, can reside upon the gas permeable material.

FIG. 2 shows an embodiment of gas permeable cell culture container 210 with lower wall support 250. Depending on the stiffness of the materials that comprise lower wall 245, it may be necessary to use lower wall support 250 to maintain lower wall 245 in a substantially horizontal position. For example, when lower wall 245 is gas permeable and comprised of a thin and flexible material, lower wall support 250 is preferably structured to maintain gas permeable lower wall 245 in a horizontal position and allow ambient gas to contact the gas permeable material. Thus, the number of contact points, distance between contact points, and amount of surface area of the gas permeable material in direct contact lower wall support 250 should be considered. Preferably, gas access openings 252 allow gas to move through lower wall support 250. Feet 251 should elevate lower wall support 250 so that ambient gas can move freely in an out of gas access opening 252. Those skilled in the art of cell culture device design will recognize that a design of a lower wall support that meets those objectives can be achieved in a wide variety of ways, some of which are described in Wilson et al. '814, Wilson et al. U.S. Pat. No. 5,693,537, Wilson et al. U.S. Pat. No. 5,714, 384, or present in the commercially available CELLine products. For cells that exhibit high oxygen demand, Wilson '848 provides additional guidance for proper structure. Although it can be permanently affixed to body 230, lower wall support 250 does not need to be. For example, when cell container 210 is disposable, it can minimize cost to make lower wall support 250 detachable and reusable. In lieu of the presence of lower wall support 250, "projections" can emanate from lower wall 245 as described in Wilson '848.

The reduction of medium temperature during shipping can decrease the metabolic demand of cells during transit. Currently, this is a typical protocol when cells or tissue are shipped. For example, in the case of human islets, the temperature of the medium is typically reduced from 37° C. to 22° C. to reduce the oxygen demand, often during culture. However, medium volume contracts during cooling, in this example by about 5%. If the device is a rigid closed body, the medium experiences a pressure drop as it attempts to contract to a smaller volume. This can degas the medium. Additionally, it places stress on the device walls. When the lower wall of the cell container is configured for gas exchange by use of material that is flexible, for example as may be the case when it is comprised of thin dimethyl silicone, the act of medium volume contracting during cooling can draw the lower wall upward. This is an undesirable position, as cells can gravitate to the perimeter of the lower wall, where they can accumulate at uncontrolled high density, potentially terminating proper nutrient transport. Medium often rises and falls in temperature during culture or shipping. Therefore, configuring the device with a cell compartment volume adjustment feature that moves to accommodate varying medium volume can help regulate pressure and prevent a lower flexible wall from being drawn into the cell compartment. The cell compartment volume adjustment feature can also mitigate any affect that pressure drop during flight may have. For example, if a drop in pressure acts to draw the walls of the cell container outward, the cell compartment volume adjustment feature can move to reduce stress on the walls of the cell container.

FIG. 3A, FIG. 3B, FIG. 3C, FIG. 3D, and FIG. 3E show an embodiment of a cell culture container configured with a cell compartment volume adjustment feature that automatically changes its position in response to pressure and/or temperature changes of medium within the cell compartment. In this illustrative embodiment, the fluid displacement member is configured to also act as a cell compartment volume adjustment feature. In the cross-sectional view of FIG. 3A, cell container 310 includes cap 325 which resides upon body 330. Cell compartment 341 occupies a volume of space within cell container 310, bounded in part by sidewall(s) 343 and lower wall 345. Cell compartment volume adjustment feature 333 resides above cell compartment 341. In FIG. 3B, cap 325 is separated from body 330 to expose cell compartment 341. Medium 315 and cells 316, in this depiction shown as a well mixed suspension, have been placed into cell compartment 341 by way of access port 340. Medium 315 initially resides at a height within cell compartment 341 that is below the height of access port 340, and more preferably below the height of cell compartment sidewall 343, thereby reducing contamination risk. As shown in FIG. 3C, cap 325 has come in contact with body 330. Cells 316 have gravitated to distribute uniformly upon lower wall 345 of cell compartment 341. Gas 320 resides above medium 315. Gas 320 also occupies overflow reservoir 335 and fluid exit path 334. Fluid exit path 334 is the space between fluid displacement member 332 and overflow reservoir 335. Fluid displacement member 332 is attached to cap 325. FIG. 3D shows fluid displacement member 332 in contact with medium 315, displacing medium 315. The upper surface of medium 315 has risen in the direction of fluid exit path 334 and a portion of gas 320 has moved out of cell compartment 341 via fluid exit path 334. In this case, although not required, cap 325 makes hermetic contact with body 330. Any of the options for handling displaced gas previously described can be used. In this depiction, cap 325 includes vent 326, which is covered by sterile filter 327. Sterile filter 327 is preferably a 0.2 micron microporous material. It can be attached to cap 325 by any method known in the art, preferably by sonic welding. Gas 320, displaced from cell compartment 341, exits cell container 310 via vent 326. In FIG. 3E, cell compartment seal 338 has made contact with sidewall 343 of cell compartment 341, closing fluid conduit 334 and preventing movement of gas and/or medium 315 into overflow reservoir 335. Overflow reservoir seal 337 ensures overflow reservoir 335 remains uncontaminated. Incompressible medium 315 exerts a force on fluid displacement member 332 when downward movement of cap 325 drives it against incompressible medium 315.

The objective of cell compartment volume adjustment feature 333 is to automatically move in response to variations in the potential energy of the fluid in cell compartment 341, as may be the case when the temperature of medium changes or walls of cell compartment 341 move outward due to pressure reduction during flight. Thus, the cell compartment volume adjustment feature requires structure that allows it to move in response to force variations that fluid within the cell compartment exerts upon it. Its potential energy is altered during the process. Skilled artisans will recognize that there are many structures available for making fluid displacement member meet its objective.

As shown in FIG. 3E, at least a portion of fluid displacement member 332 forms a boundary of cell compartment 341. The force exerted by fluid (in this case medium) within cell compartment 341 upon fluid displacement member 332, makes fluid displacement member 332 a good candidate to structure as cell compartment volume adjustment feature 333. By structuring fluid displacement member 332 is as a hermetically sealed hollow body, with walls comprised of a flexible material, similar to a balloon, it becomes cell compartment volume adjustment feature 333. Silicone provides a good material due to its biocompatibility, and excellent elongation and compression set characteristics. With this structure, as medium 315 in cell compartment 341 contracts, cell compartment volume adjustment feature 333 expands. Likewise, as medium 315 in cell compartment 341 expands, cell compartment volume adjustment 333 feature contracts.

The initial state of potential energy of cell compartment volume adjustment 333 will dictate the force that it exerts upon medium, and the pressure of the medium. Thus, a structure, or method, for controlling the initial state of potential energy is needed for optimal performance. In this illustrative embodiment, cap 325 can be threaded onto body 330 to provide structural means of placing cell compartment volume adjustment feature 333 in a desired state of initial potential energy. As cap 325 travels downward, the force exerted by medium 315 upon fluid displacement member 332 causes it to compress in volume, thereby increasing its internal pressure and its stored potential energy. Skilled artisans will recognize that precision in creating an initial desired state of potential energy can be improved by varying the geometry of various features. For example, in this illustrative embodiment, more resolution is attained as threads become finer, internal gas volume of the cell compartment volume adjustment feature becomes larger, or walls of the cell compartment volume adjustment feature become less stiff. In this depiction, the internal volume of cell compartment volume adjustment feature 333 shown in FIG. 3C, labeled V1, has been reduced in FIG. 3E, labeled V2, thereby elevating its potential energy.

A lower wall support, as previously described can be useful to prevent lower wall 343 from bowing outward if cell compartment 341 becomes pressurized, as may be the case when cell compartment volume adjustment feature 333 is in a state of elevated potential energy. If present, the lower wall support should have enough stiffness to retain the bottom of cell compartment 341 flat throughout this process. Preferably, the design ensures that as pressure increases when cell compartment volume adjustment feature 333 is driven into medium 315, it does not deflect lower wall 345 to the extent that cells pile up within the deflection area. The use of structural ribs, or other means of stiffening the lower wall support, can prevent that event.

In this state, the cell container is prepared for exposure to changing temperature and/or ambient pressure, and can automatically act to limit variations in pressure within the cell compartment. Additionally, in the medium cooling condition, undesirable position change of a flexible gas permeable lower wall, as previously described, is prevented. For example, when medium contracts during cooling, the cell compartment volume adjustment feature attempts to reduce its potential energy. The elevated internal pressure within the cell compartment volume adjustment feature will act to drive its flexible walls toward the contracting medium, thereby preventing a flexible lower wall from being drawn out of its horizontal position. In this manner, when lower wall is comprised of a thin, flexible, gas permeable material, cells can be retained in a uniform distribution upon the lower wall so long as the cell container resides in a horizontal position. In the event of medium temperature increase, the cell compartment volume adjustment feature should be capable of compressing in volume after it comes to reside in its initial position.

The fluid displacement member need not be capable of changing shape, only position, and its walls need not be flexible. For example, as shown the cross-sectional view of FIG. 4A, cell container 410 includes fluid displacement member 432, which is mounted on spring 431, to create cell compartment volume adjustment feature 433. Spring 431 is attached to cap 425. Cap 425 resides upon body 430. Cell compartment 441 occupies a volume of space within cell container 410, bounded in part by sidewall(s) 443 and lower wall 445. Cell compartment volume adjustment feature 433 resides above lower wall 445. In FIG. 4B, cap 425 is separated from body 430 to expose cell compartment 441. Medium 415 and cells 416, in this depiction shown as a well mixed suspension, have been placed into cell compartment 441 by way of access port 440. Medium 415 initially resides at a height within cell compartment 441 that is below the height of access port 440, and more preferably below the height of cell compartment sidewall 443, thereby reducing contamination risk. In FIG. 4C, cap 425 has come in contact with body 430. Cells 416 have gravitated to distribute uniformly upon lower wall 445 of cell compartment 441. Gas 420 resides above medium 415. Gas 420 also occupies overflow reservoir 435 and fluid exit path 434. Fluid exit path 434 is the space between fluid displacement member 432 and overflow reservoir 435. Preferably, to allow all gas to be removed, at least a portion of fluid displacement member 432 resides below fluid exit path 434. In FIG. 4D, cap 425 is prevented from further downward movement by body 430, spring 431 compresses as fluid displacement member 432, having driven gas from cell compartment 441, is prevented from further downward travel by the incompressible medium 415. Cell compartment volume adjustment feature 433 has been placed in a first position of stored potential energy. Cell compartment seal 438, in this depiction an o-ring, ensures medium is retained in cell compartment 441 and gas 420 within overflow reservoir 435 cannot re-enter cell compartment 441. As an alternative to the use of cell compartment seal 438, tight tolerance clearance between fluid displacement member 432 and cell compartment 441 can be used to accomplish this objective, as previously described. In this first position of FIG. 4D, cell compartment volume adjustment feature 433 is prepared to act like a piston within the cell compartment. For example, as the medium contracts during temperature reduction, force acting upon cell compartment volume adjustment feature 433 is diminished, and it is driven towards the contracting medium as spring 431 elongates, where it comes to rest in a second position of reduced potential energy, as shown in FIG. 4E. Preferably, in this second position, cell compartment volume adjustment feature 433 has some potential energy remaining so that a force is exerted upon the medium, ensuring that lower wall 445 is kept flat when it is comprised of a flexible material, as could be the case when it is gas permeable. Likewise, if medium increases in temperature, the force acting upon cell compartment volume adjustment feature 433 is increased as the potential energy of the medium increases, and cell compartment volume adjustment feature 433 moves upward to allow medium expansion, thereby alleviating pressure build up.

FIG. 5A, FIG. 5B, and FIG. 5C show yet another embodiment of the cell container configured to respond to changes in medium volume and/or ambient pressure changes. In this illustrative depiction of cell container 510, the walls of the cell compartment include a cell compartment volume adjustment feature. As shown in FIG. 5A, medium 515 and cells 516 have been introduced into cell compartment 541 via access port 540. Body 530 integrates cell compartment volume adjustment feature 533, which in this illustrative embodiment is a thin elastic material that is secured around the perimeter of body 530 in a liquid tight manner by any means commonly known in the art. An opening in body 530 exists such that medium 515 is in direct contact with cell compartment volume adjustment feature 533. Cell compartment volume adjustment feature 533 is in a first position at a first state of potential energy. Lower wall 545 is comprised of thin, flexible, gas permeable material. Lower wall support 550 maintains lower wall 545 in a flat position. In FIG. 5B, cap 525 has moved downward and fluid displacement member 532 has displaced gas 520 and a small amount of medium 515 from cell compartment 541 into overflow reservoir 535. Although tight clearance is an option, in this depiction cell compartment seal 538 prevents gas from coming back into cell compartment 541. After gas 520 has been displaced, and cap 525 attempts to move further downward, incompressible medium 515 drives cell compartment volume adjustment feature 533 to expand from its first position to a second position in order to accommodate medium 515. Cell compartment volume adjustment feature 533 in this depiction is structured as a biocompatible, elastic material, such as silicone, capable of stretching to the expanded state of the second position, which generates an increase in its potential energy and a capacity for moving back to its first position. In FIG. 5C, medium 515 has been cooled relative to its temperature in FIG. 5B. As medium 515 contracts in volume, cell compartment volume adjustment feature 533 moves towards its first shape as it seeks a reduction of potential energy. This motion helps regulate pressure and, when lower wall 545 is comprised of a flexible gas permeable material, it prevents gas permeable lower wall 545 from being drawn upward. As with the prior discussion, the shape change of the cell compartment volume adjustment feature is preferably linked to the expected volume change of the medium, and when an objective of the fluid cell compartment volume adjustment feature is to keep a flexible lower wall flat, it preferably exerts force upon the medium throughout the culture and/or shipping process. Stated differently, it retains potential energy to further reduce cell compartment volume.

Although embodiments have been depicted with a removable cap, skilled artisans will recognize that the device can be configured for closed system use. For example, medium and cells can be added by way of a septum and gas can be displaced by way of a vent. After displacing gas from the device, the device volume can be physically altered to place the cell compartment volume adjustment feature in a desired initial state of potential energy, where it seeks to automatically reduce or expand cell compartment volume depending on the anticipated temperature change, or movement of walls during pressure drop experienced during flight. In this approach, the device would include structural means for changing volume, and more specifically, for changing volume of the cell compartment. As an alternative to the inclusion of structural means for changing volume, a method of forcing medium into the cell compartment under pressure to drive the cell compartment volume adjustment feature to a desired position of potential energy can be employed.

FIG. 6A, FIG. 6B and FIG. 6C show an example of a cell container configured for closed system use in which a cell compartment volume adjustment feature and a structural means for changing the initial cell compartment volume are present. The structural means places the cell compartment volume adjustment feature in a desired state of potential energy, by which it can automatically respond to medium volume temperature and/or ambient pressure changes to mitigate unwanted pressure effects. In this illustrative embodiment, FIG. 6A shows medium 615 and cells 616 being delivered into cell compartment 641 by way of needle 671 penetrating septum 672. Gas 620 is displaced from cell compartment 641 by way of open vent 673 as medium 615 moves to occupy the entire volume of cell compartment 641. Vent 673 should be structured such that contaminants cannot enter the cell compartment 641, and be capable of being open or closed. Although vent 673 can be structured in any way that meets this purpose, such as a tortuous path, it is preferably structured to include sterile filter 675, and more preferably a hydrophobic filter with 0.2 micron porosity. Cell compartment volume adjustment feature 633 is a hollow body that includes a flexible wall(s). The hollow portion of cell compartment volume adjustment feature 633 is indicated by the symbol V1, representing its internal initial volume of gas, which is hermetically sealed within cell compartment volume adjustment feature 633. FIG. 6B shows cell compartment 641 filled with medium 615. Cells 616 have settled upon lower wall 645. Vent 673 has subsequently been closed. FIG. 6C shows cell container 610 after the potential energy of cell compartment volume adjustment feature 633 has been increased. To do so in this example, the device has integrated structural means to allow a physical reduction in height. Upper wall 676 and lower wall 645 have been driven toward each other and finger locks 678 have engaged with tangs 679 to secure cell container 610 in its new position of decreased volume. Cell compartment volume adjustment feature 633 has compressed such that its internal volume, represented by the symbol V2, is less than V1 of FIG. 6A. Any desired internal volume can be created since tangs 679 can allow discrete distances between upper wall 676 and lower wall 645 to be selected. Skilled artisans will recognize that a wide variety of ways of changing the distance between upper wall 676 and lower wall 645 can be employed. For example, the use of body walls that can move, such as by making them bellowed, in a piston style, or the like are acceptable. Skilled artisans will also recognize that a volume change of the cell compartment need not require a change in distance between upper and lower walls. For example, sidewalls can also move to force the cell compartment adjustment feature into a desired state of initial potential energy. The depicted approach is to illustrate the concept, and does not restrict the scope of the invention. After the distance between upper wall 676 and lower wall 645 has been made, the compressed gas within cell compartment volume adjustment feature 633 has increased in potential energy. In this condition, any reduction in medium volume will cause the walls of cell compartment volume adjustment feature 633 to move in the direction of the medium. When the culture or shipping environment may cause an increase or a decrease in medium volume, the stored potential energy of the cell compartment volume adjustment feature should be designed so that its stored potential energy allows it to respond to either condition. For example, in such an environment, the cell compartment volume adjustment feature of FIG. 6C would be capable of a further decrease in internal volume relative to V2 should medium temperature increase.

In the event that the device does not include structural means to place the cell compartment volume adjustment feature in a state of desired potential energy, a method of doing so can be employed. For example, referring to FIG. 6B, when medium has been introduced into cell compartment 641 such that gas has been displaced, vent 673 can be closed. Subsequently, medium can continue to be added under enough pressure to overcome the potential energy of cell compartment volume adjustment feature 633, causing it to compress in internal volume, such as that shown in FIG. 6C.

FIG. 7A, FIG. 7B, FIG. 7C, and FIG. 7D show an example of a closed system embodiment that can displace gas from the cell compartment without need of a vent. Furthermore, the overflow reservoir can also act as a cell compartment volume adjustment feature. FIG. 7A shows a cross-sectional view cell container 710 prior to use. Overflow reservoir 735 resides above cell compartment 741 and has a shape that directs fluid towards fluid exit path 734. In this case, fluid displacement member 732 is the tapered wall of overflow reservoir 735, which acts to direct gas towards fluid exit path 734 as medium enters cell compartment 741 by way of septum 772. Fluid exit path 734, residing above a portion of fluid displacement member 732, allows fluid to move from cell compartment 741 into overflow reservoir 735. FIG. 7B shows medium 715 being added to cell compartment 741 by needle 771 after it has penetrated septum 772. As medium 715 rises in height, gas 720 is compressed in volume and forced into overflow reservoir 735 by way of fluid exit path 734. The pressure exerted on the medium that is being delivered into cell compartment 741 must be greater than that of the pressure within cell compartment 741 and overflow reservoir 735 as gas is compressed. FIG. 7C shows medium 715 having come to occupy all of cell compartment 741. Gas 720 and a small amount of medium 715 have come to reside in overflow reservoir 735. The needle has been withdrawn from septum 772. The pressure in the overflow reservoir is a proportion of its gas volume relative to original volume of gas residing in the cell compartment and the overflow reservoir. Thus, backpressure on the medium as it enters the cell compartment can be altered by varying the volume of the cell compartment and/or the overflow reservoir. The pressure in the cell compartment is nearly that of the overflow reservoir. FIG. 7D shows cell container 710 oriented in a non-horizontal position, such as may be the case during shipping or handling. It can be seen that the ease at which gas 720 can contact cells residing in medium 715 has been greatly reduced relative to a conventional container that has gas and medium residing in it, such as a conical tube. By making a portion of overflow reservoir 735 flexible, such as with an elastic material such as silicone, it can respond to changes in medium volume. For example, the pressure exerted on the medium during filling can move the flexible portion of the overflow reservoir into a position where it stores potential energy. Then, if medium is reduced in temperature and contracts in volume, the flexible portion of the overflow reservoir will move towards the contracting medium. Alternatively, medium can increase in temperature and exert force upon the flexible portion of the overflow reservoir, allowing medium to increase in volume. In this manner, the overflow reservoir has become a cell compartment volume adjustment feature.

In essence, the cell compartment volume adjustment feature of any embodiments of the present invention include structural means to be capable of moving from a first position in which it stores a first amount of potential energy and defines a first volume of the cell compartment, to a second position in which it stores a second amount of potential energy and defines a second volume of the cell compartment. Among the many options for creating appropriate structural means, hollow bodies and flexible walls, springs, and elastomeric materials have been depicted. In a state of rest, the force exerted by the surrounding fluid upon the cell compartment volume adjustment feature is equal to the force that it exerts upon the surrounding fluid. Throughout this specification, reference in made to medium as the fluid exerting force. However, the fluid can be gas or liquid. Thus, the use of the term medium is non-limiting. In the condition in which fluid is increasing in temperature and volume, the cell compartment volume adjustment feature moves to allow the volume of the cell compartment to increase. In the condition in which medium is decreasing in temperature and volume, the cell compartment volume adjustment feature moves to allow the volume of the cell compartment to decrease. Preferably, the design of the cell compartment volume adjustment feature is based primarily upon the volume of the medium, and/or fluid, and the anticipated temperature change. For example, in the case where cells are cultured at 37° C. and shipped at 22° C. in a cell compartment entirely filled with medium, the volume of medium is reduced by about 5% as the temperature drops. Thus, the cell compartment volume adjustment feature, having been driven into a state of increased potential energy after medium has been added should be structured to have the capacity to move to reduce the volume of the cell compartment by 5% when medium contracts. As the cell compartment volume adjustment feature moves from the elevated potential energy state of its first position in which a first volume of the cell compartment exists, to a reduced potential energy state of its second position, in which a second volume of the cell compartment exists, the volume of cell compartment space given up by the contracting medium volume should come to be occupied by the cell compartment volume adjustment feature, preferably with minimal resultant pressure change within the cell compartment. Continuing this example, if the medium volume was 100 ml at 37° C., and a shipping temperature of 22° C. is desired, the cell compartment volume adjustment feature should be capable of moving from its first position to a second position during temperature reduction such that it displaces about 5 ml of volume from the cell compartment to accommodate the 5% loss of medium volume associated with the temperature decrease. When the lower wall is comprised of a flexible, gas permeable material, preferably the cell compartment volume adjustment feature should retain some potential energy throughout culture and/or shipping so that it exerts some force on the medium and thereby ensures that the lower gas permeable wall is held flat by the force exerted upon it by the medium. The cell compartment volume adjustment feature can also move in the opposite manner. For example, when medium temperature increases, the increase in its potential energy overcomes that of the cell compartment volume adjustment feature, causing the cell compartment volume adjustment feature to move from a first position in which a first volume of the cell compartment exists, to a second position in which a second volume of the cell compartment exists. In this manner, potential pressure build up within the cell compartment is mitigated during an increase in medium volume temperature. Preferably, the cell compartment volume adjustment feature allows the cell compartment to repeatedly increase and/or decrease in volume, thereby accommodation fluctuating ambient temperature and/or pressure changes during use.

Placing the cell compartment adjustment feature in a desired and pre-determined first state of potential energy can be achieved by including a physical structure in the device that is capable of placing the cell compartment volume adjustment feature in a desired state of potential energy. In an open system, many options exist for placing the cell compartment volume adjustment feature in such a state. A threaded cap and body can move relative to each other and provide excellent resolution for altering the potential energy of the cell compartment volume adjustment feature. In a closed system, finger locks, a piston style body, or bellowed body, are among the many structural options for physically manipulating the device to place the cell compartment volume adjustment feature in the desired state of potential energy. In the absence of physical structure to place the cell compartment volume adjustment feature in the desired state of potential energy, a non-limiting method of delivering medium at elevated pressure has been described.

Although the cell compartment volume adjustment feature has been described primarily in the context of a cell compartment entirely filled with liquid medium, skilled artisans will recognize that it can be used in the presence of liquid and/or gas. For example, there may be applications that do not benefit by the complete elimination of gas from the cell compartment, such as a variety of culture applications. The cell container is most robust if it allows cells to be cultured and shipped. This can minimize contamination risk by eliminating the need to transfer cells from a culture device to a shipping device. The optimal volume of medium may differ between the culture state and the shipping state. For example, a small amount of medium may reside at the culture state relative to the shipping state if there is a need to displace gas during shipping. This is a consideration that can affect the design of the cell compartment adjustment feature. The initial state of potential energy will differ between two identically structured cell compartment adjustment features when moved against an incompressible fluid (i.e., cell compartment filled with medium) versus a compressible fluid (i.e., cell compartment including gas). One way of configuring a cell container for optimized culture and shipping is to include two cell compartment adjustment features, one tailored to the cell culture condition and the other to the shipping condition.

If cells are cultured without medium entirely filling the cell compartment, moving the device during routine handling can allow medium to move in a type of motion that displaces cells from a uniform distribution. This can increase cell surface density (cells/cm$^2$) to an undesirable and uncontrolled level. This is more problematic when the cell compartment is cylindrical in shape, as a whirlpool motion in the liquid can more easily occur. One option is to avoid the use of a cylindrical shape. However, that may limit options for fabrication, and often cylindrical shapes are more cost effective to fabricate.

For example, standard radial seals with o-rings routinely rely on circular geometry of cylinders. Furthermore, the benefit of a conically shaped fluid displacement member and a cylindrically shaped cell compartment has been previously described. Another option is to entirely displace gas from the cell compartment, such as by use of a fluid displacement member, thereby alleviating the condition, as there is no gas-liquid interface at which waves in the medium can form. However, addressing this problem by filling the device entirely with medium may not an optimal solution when the cost of the medium is high, or when there is a desire to keep the same ratio of medium volume to cell number as that of traditional flask culture. Yet another option is to pressurize the gas by use of an appropriately structured cell compartment adjustment feature so that the wave formation is diminished relative to that formed in the presence of a vented cell compartment. In this approach, the optimal pressure would best be determined by trial and error.

Figure 8B:
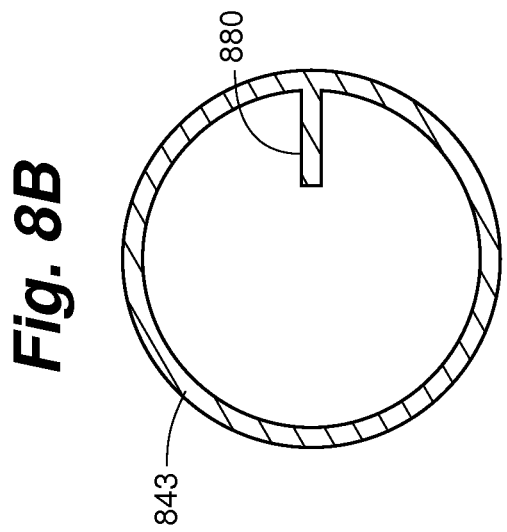
FIG. 8B shows cross-section A-A of FIG. 8A.
Figure 8A:
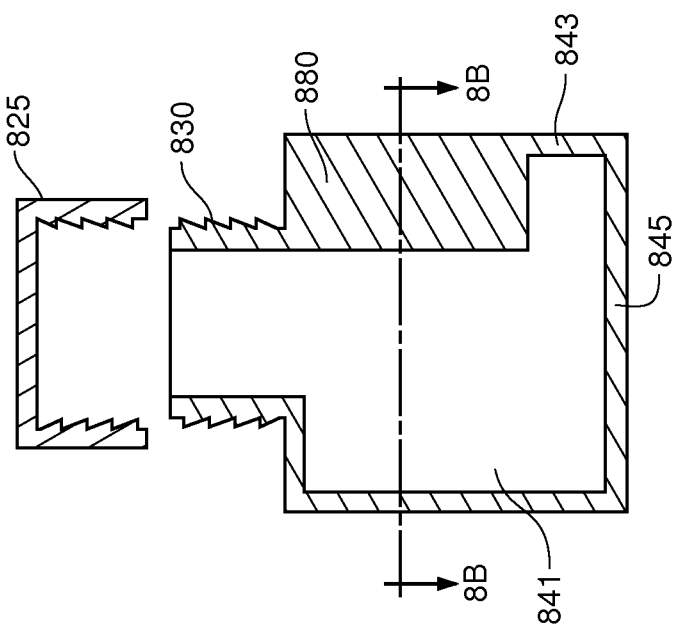
FIG. 8A shows a cross-sectional view of a cell container in which a baffle resides in the cell compartment.

Another preferred option is depicted in FIG. 8A and FIG. 8B, which illustrate an embodiment of a cell container that includes a baffle to restrict medium motion when if there is gas residing in the device, as may be the case when used for culture, thereby minimizing the potential displacement of cells from their uniform distribution and allowing a wider range of culture protocols. The cross-sectional view of FIG. 8A shows cap 825 removed from body 830, and baffle 880 residing within culture compartment 841. Cross-section A-A is shown in FIG. 8B. Baffle 880 projects into culture compartment 841, in this case from sidewall 843. In this depiction, culture compartment 841 is a cylindrical in shape. Baffle 880 can obstruct the rotation of medium during routine handling. Thus, medium need not displace the gas to prevent cells from being subjected to the forces of medium rotation. The baffle can make contact with lower wall 845, or extend from lower wall 845. Preferably, a gap exists between baffle 880 and lower wall 845 to facilitate the ease at which cells can be recovered from the device. The gap allows users to recover cells by tilting the device and pipetting from any location, as cells and medium are free to pass under the baffle. The gap between the lowest portion of baffle 880 and lower wall 845 should be selected based on the anticipated medium height. For example, if medium is to reside at a height of 1.0 cm, the distance between lower wall 845 and baffle 880 should be less than 1.0 cm. In that manner, the baffle is in contact with medium during culture. However, if the device is not gas permeable, the baffle should preferably make contact with the lower wall since the normal height of medium in cultures that rely on a gas-liquid interface for gas exchange is about 2 mm to 3 mm. Thus, even a small gap between the baffle and the lower wall may not prevent cells from being redistributed to high surface density. In a preferred embodiment, the baffle is a vertical wall that projects from the cell compartment wall a distance that does not exceed 50% of the distance between opposing cell compartment walls.

Figure 9A:
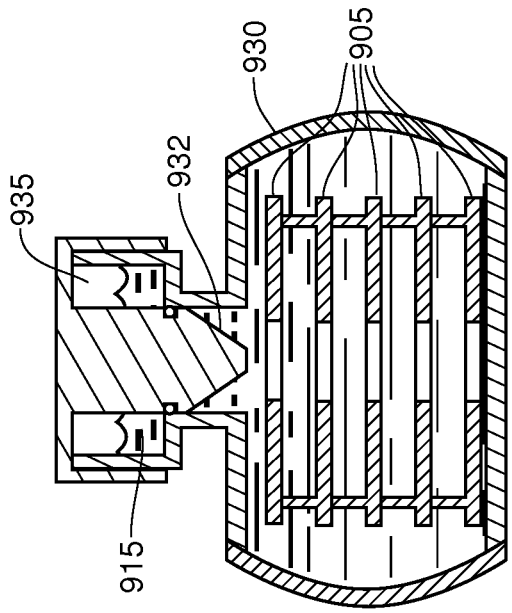
FIG. 9A shows a cross-sectional view of a cell container that includes multiple scaffolds, residing on above the other. The cap, disconnected from the body, includes a fluid displacement member. The body includes an overflow reservoir and is structured in part with elastic walls.
Figure 9B:
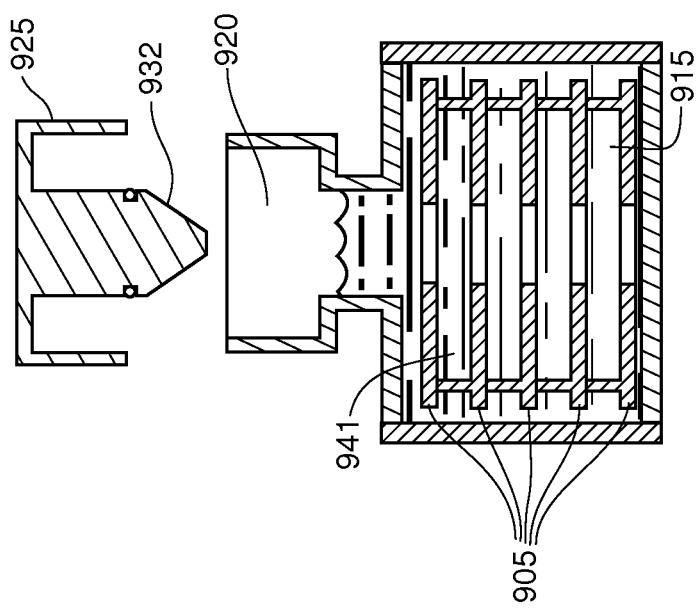
FIG. 9B shows the cap attached to the body. The fluid displacement member has driven gas from the cell compartment. A small amount of medium resides in the overflow reservoir. The force exerted by the fluid displacement member on the medium has driven the cell compartment volume adjustment feature, in this case the elastic walls, to a desired state of potential energy.

There may also be a desire to ship, or culture and ship, a large quantity of cells that prefer to be attached to a surface, or prefer to reside at a low surface density. In this event, the cell compartment can integrate numerous attachment surfaces for cells to reside upon. FIG. 9A and FIG. 9B show an embodiment that integrates scaffolds residing one above the other. Wilson et al. '814 provides guidance for how to best achieve this geometry. Although the scaffolds can be any material, polystyrene is a good choice because it is inexpensive and easy to fabricate. The scaffolds may or may not be tissue culture treated depending upon whether the cells are suspension or adherent cells. The device can be constructed with a fluid displacement member and/or a cell compartment volume adjustment feature. Preferably, when the application includes a culture stage or oxygen availability is desired during transit, the device body is comprised of gas permeable material. Although any structure that skilled artisans employ as a cell compartment volume adjustment feature can be integrated, when the body is comprised of gas permeable material, it can also act as a cell compartment volume adjustment feature. In the illustrative embodiment of FIG. 9A, a stack of vertically arranged, scaffolds 905 reside within cell compartment 941. Gas 920, medium 915, and cells reside within cell compartment 941. Cap 925, configured as with fluid displacement member 932, has not yet been attached. To allow the gas permeable walls of the device to move in response to temperature increases or decreases, it is best to fabricate them at least in part of flexible material and to leave some distance between the edge of the scaffolds and the flexible portion of the device wall. Although this distance is not necessary, it increases the capacity for flexible walls to move inward if medium volume contracts. However, an initial distance can be established by the simple act of placing a cap on the device. In FIG. 9B, fluid displacement member 932 and has displaced gas and driven a small amount of medium 915 into overflow reservoir 935. A portion of the walls of body 930, flexible and preferably gas permeable, have been distended to a position of increased potential energy, but remain capable of further distention and further increase in potential energy should medium temperature increase. The walls are capable of moving towards the scaffolds should medium temperature decrease. Silicone is a good choice of material for the portion of the walls that are intended to move. It is gas permeable, flexible, and highly elastic. If silicone resides in the device, care should be taken to ensure that the surface chemistry of scaffolds 905, if tissue treated, is not altered during gamma or e-beam exposure by employing the methods described in co-pending Wilson et al. '856.

Figure 10A:
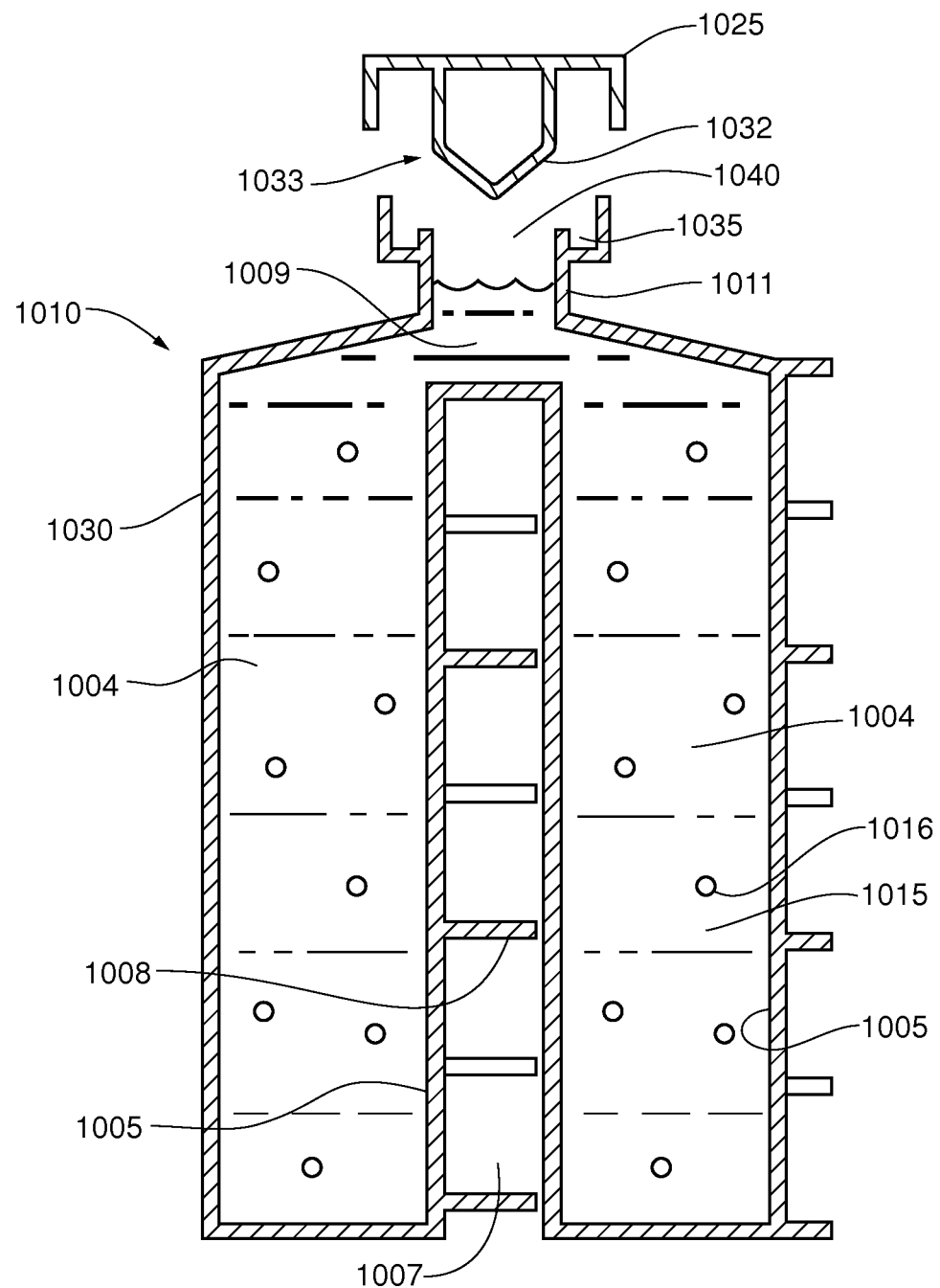
FIG. 10A shows a cross-sectional view of a cell container that includes two gas permeable cell compartments, residing one above the other separated by a gas space. A manifold connects the cell compartments. The cap, disconnected from the body, includes a cell compartment volume adjustment feature that includes a fluid displacement member. Medium and cells, in suspension, reside in the cell culture compartments. The access port includes an overflow reservoir.
Figure 10B:
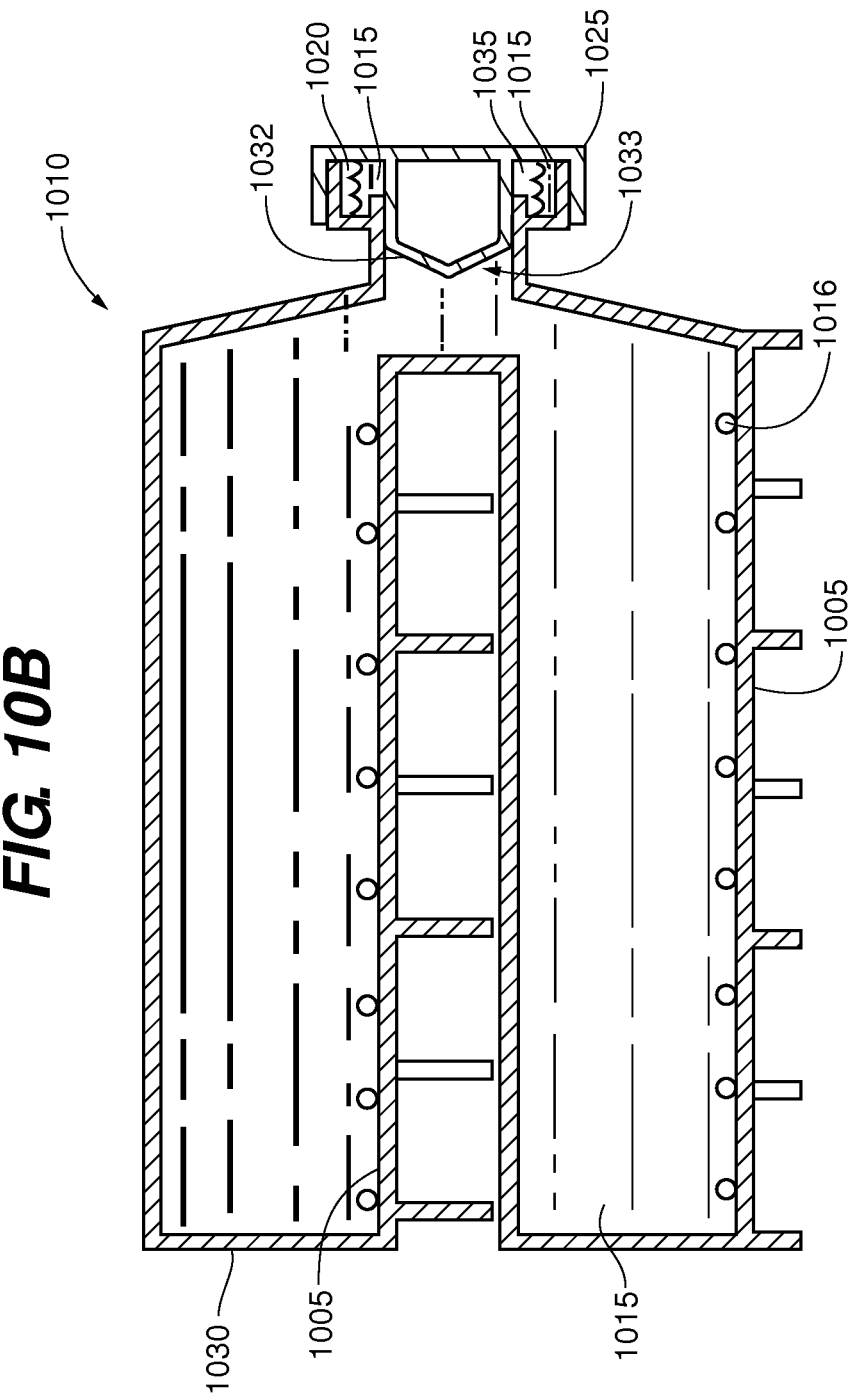
FIG. 10B shows the cap attached to the body. Gas has been displaced from the cell compartment and medium fills it entirely. A small amount of medium resides in the overflow reservoir. Cells are distributed uniformly about the lower walls of the cell compartments. The fluid displacement member has been compressed to assume a desired state of potential energy.

There may also be a desire to culture and/or ship cells that prefer to be reside in a condition where the ratio of gas permeable surface area to scaffold surface area exceeds that of the illustrative embodiment of FIG. 10A and FIG. 10B. For example, shipping very large quantities of islets can be achieved in a device with multiple layers of gas permeable surfaces for them to reside upon. FIG. 10A and FIG. 10B show an illustrative embodiment of how this can be achieved. Reference to Wilson '848 provides further guidance. In FIG. 10A, two cell compartments 1004 reside one above the other connected by manifold 1009. Any of the walls of device body 1030 can be comprised of gas permeable material, as described in Wilson '848. A gas space 1007 separates cell compartments 1004. Scaffold supports 1008 act to retain scaffolds 1007 in a substantially flat state. Cap 1025 is unattached. Cell container 1010 is oriented such that cells 1016 and medium 1015 have been introduced into cell compartments 1004. Medium resides at a level below the entrance to access port 1040. Cell compartment volume adjustment feature 1033, attached to cap 1025, includes a tapered wall, forming fluid displacement member 1032. Neck 1011 included overflow reservoir 1035. In FIG. 10B, cell container 1010 has been oriented such that cells 1016 and medium 1015 have come to reside above scaffolds 1005. Cap 1025 has sealed against body 1030, and gas 1020 and a small amount of medium 1015 have been displaced by fluid displacement member 1032 into overflow reservoir 1035. In this depiction, the fluid displacement member has been configured as a hollow body with flexible walls so as to also function as cell compartment volume adjustment feature 1033. As described previously, cell compartment volume adjustment feature 1033 is capable of distending or retracting in response to medium volume changes.

The use of a fluid displacement member can be very useful for certain devices designed for cell culture that function better when gas is either not present, or is isolated to specific areas within the device. For example, U.S. patent applications Ser. Nos. 11/454,964 and 11/478,823 describe geometric features that can minimize the migration of gas into unwanted areas of a cell culture device by manipulating the position of the device to trap gas. Skilled artisans will recognize that the fluid displacement member of this invention is useful for displacement of gas from devices that are used to culture cells, such as those depicted in '964 and '823, and the commercially available Hyperflask™ produced by Corning®. Thus, a preferred method of preventing gas from entering areas of a cell culture device in which it is unwanted is to structure such a cell culture device with a cap that includes a fluid displacement member and an access port that includes an overflow reservoir. The cell container (i.e., the cell culture device) could then be used as follows. Orient the access port is in a position where medium will not spill out of the device, introduce cells and medium into the cell culture device, and attaching the cap onto the device such that it covers the access port, thereby allowing gas to be displaced from the cell compartment by the fluid displacement member. The device can then be re-oriented to a position such that scaffolds are horizontal and placed in an atmosphere suitable to cell survival. In a more preferred method, the cell container device access port is oriented vertically so that it allows medium to be added to the device while the device resides in the culture position (i.e., horizontally), thereby allowing simpler automation or single handed filling.

The use of a cell compartment volume adjustment feature described herein can be very useful for certain devices designed for cell culture that are best operated when gas is prevented from being in proximity of cells, or forming within the medium. Gas can come to reside in unwanted areas when medium temperature is altered during culture, as may be the case when cold medium is added to a device and is subsequently warmed in an incubator, which can reduce gas carrying capacity and cause bubble formation. The cell compartment volume adjustment feature described herein can be used to pressurize the medium in order to prevent this type of event. To do so, the cell compartment volume adjustment feature should be structured such that it arrives at a state of elevated potential energy when medium is increased in temperature and exerts a force upon the medium that regulates pressure of the medium such that degassing is prevented or minimized. Thus, in a cell culture application, one would structure the cell compartment volume adjustment feature to be capable of regulating the pressure of the medium, integrating it into a cell culture device, placing medium and cells into the cell culture device, and incubating the device to culture cells.

During shipping, maintaining the cell container in a horizontal position is preferred, as it allows cells to reside in a uniform distribution. This can be useful in preventing any damage that can occur when cells are allowed to gravitate to very high density, such as may occur when cells settle into a corner of the device. U.S. Pat. No. 6,490,880 and U.S. patent application Ser. No. 10/829,752 describe the use of gimbal mechanisms to keep a device oriented in a horizontal position during shipping. A preferred method of shipping the cell container places its lower wall and/or the scaffolds in a horizontal position throughout transit. In this orientation, cells can remain uniformly distributed at a desired surface density. Thus, one method of using the cell container would be to structure it with a fluid displacement member to displace gas and/or a cell compartment volume adjustment feature to compensate for variations in medium volume, introduce medium and cells, optionally perform cell culture, subsequently place the cell container in a gimbal mechanism, and ship the cell container to a desired destination.

Skilled artisans will recognize that a wide variety of published information is available for guidance in the specific choice of material selection for various aspects, features, or components of the present invention. All materials used for cell culture devices or for containers that house biological materials are options. USP Class VI materials that can be gamma irradiated are preferred.

The invention will be further described with reference to the following non-limiting Examples.

EXAMPLES

Example 1

A cell culture container with fluid displacement member was structured as follows and is depicted according to FIG. 11. Cap 1125, integrated fluid displacement member 1132, dimensioned as shown. Body 1130 was fabricated of clear polycarbonate rod stock. Cell compartment 1141 was made by machining a cylindrical opening in body 1130, 1.40 inches in diameter and 2.46 inches in height. Lower wall 1145 was fabricated of dimethyl silicone, 70 shore A durometer, and 0.004 inches thick, and was attached to body 1130 by compression from polycarbonate lower wall support 1150, The gas permeable silicone lower wall 1145 formed a surface area of 10 cm². Lower wall support 1150 was 0.13 inch thick in areas directly below lower wall 1145, was attached to body 1130 with 8 screws, uniformly spaced about the perimeter of body 1130. A 50 ml pipette was used to place 40 ml of medium into cell compartment 1141. Medium temperature was about 37° C. Medium came to reside at a height of 1.58 inches above lower wall 1145 and at a height of 0.36 inches below the highest portion of cell compartment sidewall 1143. Cap 1125 was screwed onto body 1130 until overflow reservoir seal 1137 prevented further rotation. Cell compartment seal 1138 prevented fluid from moving into or out of cell compartment 1141. At the time that further travel of cap 1125 ceased, the closest point of fluid displacement member 1132 to lower wall 1145 was 1.2 inches. A visual inspection through clear cell compartment wall 1143 showed that all gas had been displaced from cell compartment 1141 and a small amount of medium had been moved into overflow reservoir 1135 by moving through fluid exit path 1134. Subsequently, to demonstrate the problems of temperature change, medium was reduced in temperature from its initial temperature of about 37° C. to about 22° C. As medium contracted, gas permeable lower wall 1145 was observed to be drawn from a flat position towards fluid displacement feature 1132. This example demonstrates how gas can be displaced from a cell container without need of filling it entirely with medium, but how temperature changes in the medium can affect the optimal orientation of a lower wall comprised of thin gas permeable material.

Example 2

A test was conducted to demonstrate the capacity of a cell compartment volume adjustment feature to respond to changes in medium temperature resulting from temperature change. A test device was constructed as shown in FIG. 12, cap 1225, integrated a hollow fluid displacement member 1232 formed of flexible silicone walls, 70 Shore A durometer, thereby creating cell compartment adjustment feature 1233. The profile of fluid displacement member 1232 was dimensioned as described in Example 1. Wall thickness of the hollow cell compartment adjustment feature 1233 was uniform and 0.10 inch. The body of the cell container, including cell compartment 1241, lower wall 1245, lower wall support 1250, and overflow reservoir 1235, were structured according to Example 1. As described in Example 1, 40 ml of medium was placed into cell compartment 1241. Medium and gas within the device were at about 37° C. Cap 1225 was screwed onto body 1230 until overflow reservoir seal 1237 prevented further rotation. Cell compartment seal 1238 prevented fluid movement into or out of cell compartment 1241. All gas and a small amount of medium was observed to be displaced into overflow reservoir 1235. The internal volume of cell compartment volume adjustment feature 1233 was compressed to a pressure of about 3.0 P.S.I. as measured by a sphygmomanometer hermetically attached to test orifice 1239. The cell container was placed in an ambient atmosphere of about 22° C. As medium came to that temperature, pressure in within the internal volume of cell compartment volume adjustment feature 1233 was reduced to about 2.0 P.S.I. as cell compartment volume adjustment feature 1233 distended into cell compartment 1241 to occupy the volume of space given up by the contracting medium. Lower wall 1245 remained flat, as opposed to the bowed shape at which it came to in Example 1. This demonstrated the capacity of the cell compartment volume adjustment feature to automatically move from a position of a first stored potential energy to a second position of reduced, but positive potential energy, in order to prevent unwanted effects from temperature change, including the ability to maintain a lower wall comprised of thin gas permeable material in a flat state.

Those skilled in the art will recognize that numerous modifications can be made thereof without departing from the spirit. Therefore, it is not intended to limit the breadth of the invention to the embodiments illustrated and described. Rather, the scope of the invention is to be interpreted by the appended claims and their equivalents.

What is claimed is:
1. A cell container comprised of:
   a cell compartment, said cell compartment bounded at least in part by a sidewall and a bottom, and
   an access port, and
   an overflow reservoir and a fluid exit path connecting said cell compartment to said overflow reservoir, and
   a fluid displacement member capable of terminating fluid flow to said overflow reservoir, and
   means for adjusting the position of said fluid displacement member relative to the said cell compartment so that in use the fluid displacement member moves into said cell compartment when the fluid residing in said cell compartment decreases in volume.
2. A cell container comprised of:
   a cell compartment occupying a volume of space and bounded in part by a sidewall and a bottom, and
   at least a portion of said bottom being comprised of gas permeable material and said gas permeable material being flat during use, and
   an access port, and
   a cell compartment volume adjustment feature, and
   during use said volume adjustment feature is able to change its position when the temperature of medium is decreased and thereby exerting a force on the fluid within the cell compartment that is great enough to keep said gas permeable material flat during a decrease in media temperature.

3. A container comprising:
a cap, a cell compartment that occupies a volume of space, and a cell compartment volume adjustment feature; and
said cell compartment adjustment feature incapable of allowing media to pass through it during use and including means for altering the volume of said cell compartment and to place said cell compartment adjustment feature into an initial state of potential energy that decreases as the cell compartment volume decreases.

4. The device of claim 1 wherein said cell compartment is comprised of gas permeable material.

5. The device of claim 1 wherein said gas permeable material is comprised of silicone.

6. The device of claim 1 wherein said fluid displacement member has a shape that includes a tapered wall that directs fluid towards the perimeter of said cell compartment.

7. The device of claim 6 wherein said fluid displacement member is in the shape of a cone.

8. The device of claim 1 wherein said fluid displacement member is hollow.

9. The device of claim 1 wherein said cell culture compartment is capable of holding media such that the highest location of the media is at a height that exceeds 2.0 cm from the lowest location of the media.

10. The device of claim 2 including a lower wall support in contact with at least a portion of said gas permeable material.

11. The device of claim 2 wherein said gas permeable material is comprised of silicone.

12. The device of claim 2 wherein said volume adjustment feature has a shape that includes a tapered wall that directs fluid towards the perimeter of said cell compartment.

13. The device of claim 2 wherein said volume adjustment feature member is hollow.

14. The device of claim 6 wherein said cell culture compartment is capable of holding media such that the highest location of the media is at a height that exceeds 2.0 cm from the lowest location of the media.

15. The device of claim 3 wherein said cell compartment is comprised of gas permeable material.

16. The device of claim 3 including a support is in contact with at least a portion of said gas permeable material.

17. The device of claim 15 wherein the gas permeable material is comprised of silicone.

18. The device of claim 3 wherein said cell compartment volume adjustment feature has a shape that includes a tapered wall that directs fluid towards the perimeter of said cell compartment.

19. The device of claim 3 wherein said cell compartment volume adjustment feature is hollow.

20. The device of claim 3 wherein said cell culture compartment is capable of holding media such that the highest location of the media is at a height that exceeds 2.0 cm from the lowest location of the media.

* * * * *